US009983056B2

(12) United States Patent
Froehlich et al.

(10) Patent No.: US 9,983,056 B2
(45) Date of Patent: May 29, 2018

(54) OPTIMIZATION OF THE LASER OPERATING POINT IN A LASER ABSORPTION SPECTROMETER

(71) Applicant: Thermo Fisher Scientific (Bremen) GmbH, Bremen (DE)

(72) Inventors: Ulf Froehlich, Bremen (DE); Eric Wapelhorst, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 95 days.

(21) Appl. No.: 15/251,952

(22) Filed: Aug. 30, 2016

(65) Prior Publication Data

US 2017/0059403 A1 Mar. 2, 2017

(30) Foreign Application Priority Data

Sep. 2, 2015 (GB) .................................. 1515553.4

(51) Int. Cl.
*G01N 21/00* (2006.01)
*G01J 3/02* (2006.01)
(Continued)

(52) U.S. Cl.
CPC ............. *G01J 3/027* (2013.01); *G01J 1/4257* (2013.01); *G01J 3/26* (2013.01); *G01J 3/42* (2013.01);
(Continued)

(58) Field of Classification Search
None
See application file for complete search history.

(56) References Cited

U.S. PATENT DOCUMENTS 4,730,112 A * 3/1988 Wong .................... G01J 3/4338 250/341.1
5,202,560 A 4/1993 Koch et al.
(Continued)

FOREIGN PATENT DOCUMENTS

DE 102011077634 A1 12/2012
WO 03069742 A1 8/2003

OTHER PUBLICATIONS http://www.laserfocusworld.com/articles/print/volume-51/issue-05/features/nonlinear-optics-ppln-waveguides-perform-quantum-frequency-conversion.html, downloaded Aug. 24, 2016.
(Continued)

*Primary Examiner* — Kara E Geisel
*Assistant Examiner* — Jarreas C Underwood

(57) ABSTRACT

An operating value of a first laser parameter of a laser device in a laser absorption spectrometer is optimized. The wavelength of laser device emitted light is adjusted by the first or a second laser parameter. The laser absorption spectrometer comprises a light intensity detector measuring the laser light intensity from the laser device. For each of multiple values of the first laser parameter: the light intensity detector measures light intensity obtained across a range of second laser parameter values, and an extremum in the light intensity measure and a peak position for the extremum are identified. A range of first laser parameter values is identified within the values of the first laser parameter for which there is a continuous trend in changes to the identified peak position with changes to the first laser parameter. The first laser parameter operating value is set to be within the identified range.

22 Claims, 11 Drawing Sheets

(51) Int. Cl.

| | |
|---|---|
| ***G01J 3/433*** | (2006.01) |
| ***H01S 5/06*** | (2006.01) |
| ***H01S 5/062*** | (2006.01) |
| ***G01J 1/42*** | (2006.01) |
| ***G01J 3/26*** | (2006.01) |
| ***G01J 3/42*** | (2006.01) |
| ***H01S 5/068*** | (2006.01) |
| ***H01S 5/0683*** | (2006.01) |
| *H01S 5/00* | (2006.01) |
| *H01S 5/12* | (2006.01) |
| *H01S 5/40* | (2006.01) |
| *G01N 21/39* | (2006.01) |

(52) U.S. Cl.

CPC .............. *G01J 3/433* (2013.01); *G01N 21/39* (2013.01); *H01S 5/0612* (2013.01); *H01S 5/0622* (2013.01); *H01S 5/0683* (2013.01); *H01S 5/06804* (2013.01); *H01S 5/06808* (2013.01); *G01J 2003/4334* (2013.01); *G01N 21/00* (2013.01); *G01N 2021/399* (2013.01); *H01S 5/005* (2013.01); *H01S 5/0092* (2013.01); *H01S 5/0617* (2013.01); *H01S 5/12* (2013.01); *H01S 5/4087* (2013.01)

(56) References Cited

U.S. PATENT DOCUMENTS

| | | | | |
|---|---|---|---|---|
| 6,750,972 | B2 * | 6/2004 | Sandstrom ............ | G01J 1/4257 356/454 |
| 7,386,020 | B2 * | 6/2008 | Chieng ............... | H01S 5/06804 372/29.015 |
| 7,391,795 | B2 * | 6/2008 | Yumoto ................. | G01N 21/39 372/21 |
| 7,609,736 | B2 * | 10/2009 | Difazio .............. | G06K 7/10851 372/38.01 |
| 7,634,197 | B2 * | 12/2009 | Nelson ................. | H04B 10/504 372/33 |
| 7,668,216 | B2 * | 2/2010 | Colbourne ............ | H01S 5/0622 372/29.015 |
| 8,000,367 | B2 * | 8/2011 | Yang ..................... | H01S 5/3402 372/45.01 |
| 2004/0027575 | A1 * | 2/2004 | Von Drasek .......... | H01S 5/1032 356/432 |
| 2012/0287418 | A1 * | 11/2012 | Scherer .................. | G01N 21/61 356/51 |
| 2017/0276831 | A1 * | 9/2017 | Galford .................. | G01V 13/00 |

OTHER PUBLICATIONS http://www.rp-photonics.com/periodic_poling.html, downloaded Aug. 24, 2016.

Lightwave Application Note #8, 13 pages, 2005.

Richter et al., "High-precision CO2 isotopologue spectrometer with a different-frequency-generation laser source," Opt. Lett., 34, 172-174, 2009.

Rudder et al., "Hybrid ECL/DBR wavelength & spectrum stabilized lasers demonstrate high power & narrow spectral linewidth," Proc. SPIE 6101, 610101-610108, 2006.

* cited by examiner

OPTIMIZATION OF THE LASER OPERATING POINT IN A LASER ABSORPTION SPECTROMETER

CROSS-REFERENCE TO RELATED APPLICATION

This application claims the priority benefit under 35 U.S.C. § 119 to British Patent Application No. 1515553.4, filed on Sep. 2, 2015, the disclosure of which is incorporated herein by reference.

TECHNICAL FIELD

The present disclosure relates to a method and apparatus for optimizing an operating value of a first laser parameter of a laser device in a laser absorption spectrometer.

BACKGROUND

Laser absorption spectrometry (LAS) may be used to assess the concentration or amount of a species in gas phase by absorption spectrometry. As well as quantitative assessments of the amounts of different atoms and molecules in the gas phase, LAS can also be used for isotope ratio measurements based on absorption by isotopologues of the same molecule. Such application of LAS is called Isotope Ratio Optical Spectrometry (IROS). For example, $^{13}C$:$^{12}C$ and $^{18}O$:$^{16}O$ isotope ratios in a sample of $CO_2$ gas may be assessed.

In LAS, the light emitted from a laser source is passed through the gas to be analysed to a detector that measures the intensity of received laser light. The wavelength of the laser light is scanned across the absorption peaks of an atomic or molecular species in the gas. An absorption peak of a species occurs at a wavelength (a peak position) at which the light is absorbed by the species. A reduction in the measured signal intensity at a characteristic peak position (i.e., at a characteristic wavelength) may indicate the presence and/or concentration of a particular species. In the case of IROS, each isotopologue of the species has at least one characteristic peak position. A reduction in the measured signal intensity at a characteristic peak position may indicate the presence of a particular isotopologue, and the extent of the reduction may be used to determine the concentration of that isotopologue and/or an isotope ratio in that species. For example, $CO_2$ isotopologues $^{12}C^{16}O^{16}O$, $^{13}C^{16}O^{16}O$ and $^{12}C^{18}O^{16}O$ each have different absorption peaks at specific wavelengths due to quantum mechanical rotational-vibrational states (i.e., each isotopologue absorbs different wavelength light). Measuring the different absorption peaks of two or more isotopologues can be used to determine an isotope ratio such as $^{13}C$:$^{12}C$ or $^{18}O$:$^{16}O$ in the $CO_2$.

The laser source used in LAS may comprise at least one laser diode. The wavelength of light emitted from the laser diode may be altered, or tuned, by changing at least one laser parameter. The wavelength of light emitted from the laser diode may therefore be scanned across a range of wavelengths by changing at least one laser parameter. The laser parameters may comprise the laser diode temperature and/or the injection current, also termed drive current, to the laser diode.

For each wavelength to which the laser is tuned when being scanned across the absorption peaks of a species, it is preferable for the laser to operate at a single optical frequency (i.e., at any single moment, the laser operates at a single optical frequency). Furthermore, it is also desirable that as the wavelength of the laser light is scanned across the absorption peaks, the wavelength is tuned (i.e., increased or decreased) continuously and predictably. In practice, this may not be possible due to mode hopping and/or multimoding, as explained in the document ILX Lightwave, Mode Hopping In Semiconductor Lasers, Application Note #8 (2005), which is available at http://assets.newport.com/web-Documents-EN/images/AN08_Mode_Hopping_Laser_Diode_IX.PDF. Multimoding is where the laser diode outputs multiple optical frequencies associated with different resonator modes. Mode hopping is where the laser diode exhibits sudden, unpredictable jumps of the wavelength associated with different resonator modes.

To achieve single-frequency operation and continuous, predictable wavelength tuning, both multimode operation and discontinuities in wavelength caused by switching between different resonator modes should be avoided. During initial calibration of a laser absorption spectrometer, the operating point of the laser diode, which is defined by the laser parameters, may be set with this in mind.

Typically, an optical spectrum analyser is used to measure the wavelength of the laser light and judge if the laser diode is operating at a single optical frequency. A laser parameter map is generated by varying the laser parameters, measuring the wavelength of the laser light at each combination of parameters and judging if the laser diode is operating at a single optical frequency at each combination of parameters. Stable regions of the laser parameter map may then be identified and the operating point of the laser diode (i.e., the particular laser parameter values around which the laser will operate) is chosen to be in the centre of a stable region of the laser parameter map.

However, the stable regions may change as a laser ages. Consequently, over time, the stable regions on the laser parameter map may move such that the operating point of the laser diode is no longer in the centre of the stable region and may be towards a discontinuity and/or a region of multimoding. If this happens, during operation of the laser absorption spectrometer, as the wavelength of the laser light is varied across the absorption peaks of a species, at times the laser light might not operate at a single optical frequency and/or the wavelength might not tune continuously and predictably. This may result in errors and inaccuracies in measurements from the laser absorption spectrometer.

Consequently, it is desired to have an efficient procedure for re-optimizing the operating point of a laser built into a laser absorption spectrometer with respect to stability.

SUMMARY

The present disclosure provides a method for optimizing an operating value of a first laser parameter of a laser device in a laser absorption spectrometer, wherein the wavelength of laser light emitted from the laser device is variable by adjusting either of the first laser parameter and a second laser parameter of the laser device, and wherein the laser absorption spectrometer comprises a light intensity detector configured to measure the intensity of laser light received from the laser device, the method comprising: for each of a plurality of values of the first laser parameter: obtaining a measure of light intensity received at the light intensity detector across a range of values of the second laser parameter (which may be a continuous range or a contiguous range); identifying an extremum (for example, a maximum or minimum) in the measure of light intensity; and; identifying a peak position for the extremum; identifying a range of values of the first laser parameter within the plurality of values of the first laser parameter for which there is a continuous trend in changes to the identified peak position with changes to the first laser parameter; and setting the operating value of the first laser parameter to be within the identified range of values of the first laser parameter.

Thus, the operating point of the laser device may be optimized with respect to stability at any time during the lifetime of the laser absorption spectrometer. Thus, as the laser device ages, its optimum operating point may be adjusted to ensure that it remains in a stable, single-frequency region, thereby maintaining the accuracy of measurements from the laser absorption spectrometer over time.

The method could be run on the laser absorption spectrometer on a regular basis, the regularity of which could be chosen by the user. For example, the process could be arranged to be automatically run once a month, or more or less frequently than this. In this way, the operating point of the laser device can be automatically maintained at or close to optimum as the laser device ages.

Preferably, the identified range of values of the first laser parameter is a range of values of the first laser parameter within the plurality of values of the first laser parameter for which a function defining the identified peak positions with changes to the first laser parameter is a continuous function. A continuous function is a function for which a small change in the input to the function (in this case, the first laser parameter) results in a small change in the output to the function (in this case, the identified peak position).

The continuous trend may be a linear, or near-linear, i.e., substantially linear (for example, linear to within a tolerance value) continuous trend.

Preferably, the identified peak position is based at least in part on a value of the second laser parameter corresponding to the identified extremum. In this case, the peak position is the value of the second laser parameter at which the extremum was identified. By identifying the peak position in this way, an absolute peak position is determined, irrespective of whether or not the laser device is multimoding.

Alternatively, the peak position may be indicative of a relative wavelength, wherein the relative wavelength is the wavelength of the laser light at the identified extremum relative to a reference wavelength in a range of wavelengths across which the laser light is scanned by the range of values of the second laser parameter. The reference wavelength may be the maximum or minimum of the range of wavelengths.

Preferably, the method further comprises: identifying a range of values of the first laser parameter within the plurality of values of the first laser parameter for which: there is a continuous trend in changes to the identified peak position with changes to the first laser parameter; and a peak strength for each of the identified extrema is the same to within a threshold tolerance. By also considering peak strength, multimoding may be identified without requiring an etalon or knowing anything about the size and position of the spectral window of the laser absorption spectrometer, which might require a comparison of the identified peak positions and the corresponding peak strengths with a theoretical spectrum of the sample gas. Thus, regions of multimoding may be more straightforwardly identified.

The peak strength may be based at least in part on, at least one of the peak height and/or the peak area. For example, it may be the peak height, or the peak area, or a value derived at least in part from at least one of the peak height and/or the peak area.

The method may further comprise: identifying a range of values of the first laser parameter within the plurality of values of the first laser parameter for which: there is a continuous trend in changes to the identified peak positions with changes to the first laser parameter; and the number of identified extrema at each of the plurality of values of the first laser parameter corresponds with an expected number of extrema. The expected number of extrema may be determined, for example, from a comparison of the identified peak positions and the corresponding peak strengths with a theoretical spectrum of the sample gas, or by using an etalon to generate the extrema in the received laser light.

Preferably, the extremum is identified using a peak-find algorithm. The peak-find algorithm may find the peaks by taking the first derivative of the measure of light intensity received at the light intensity detector.

Two or more ranges of values of the first laser parameter may be identified within the plurality of further values of the first laser parameter and the method may further comprise: setting the operating value of the first laser parameter to be within the largest of the two or more identified ranges of values of the first laser parameter. The first laser parameter may be set to a value that is closer to the centre of the identified range of values of the first laser parameter than it is to either limit of the identified range of values of the first laser parameter. Additionally, or alternatively, the operating value of the first laser parameter may be set to within a tolerance threshold of the centre of the identified range of values of the first laser parameter. By setting the operating value in this way, the operating value may stay within a stable operating region of the laser device for longer over time, thus enabling reliable measurements to be taken from the laser absorption spectrometer for a longer period of time.

The laser device may comprise a laser diode, wherein: the first laser parameter is a temperature of the laser diode and the second laser parameter is an injection current of the laser diode; or the first laser parameter is an injection current of the laser diode and the second laser parameter is a temperature of the laser diode.

The laser device may comprise a first laser diode and a second laser diode configured together to produce the laser light emitted from the laser device (for example, using difference frequency generation or sum frequency generation), the first laser parameter being a parameter of the first laser diode and the second laser parameter being a parameter of the second laser diode. The first laser parameter may be an injection current to the first laser diode and the second laser parameter may be an injection current to the second laser diode. Alternatively, the first laser parameter may be a temperature of the first laser diode and the second laser parameter may be an injection current to the second laser diode. Alternatively, the first laser parameter may be an injection current to the first laser diode and the second laser parameter may be a temperature of the second laser diode. Alternatively, the first laser parameter may be a temperature of the first laser diode and the second laser parameter may be a temperature of the second laser diode. The first laser diode may be a wavelength stabilised laser diode and the second laser diode may be a distributed feedback laser diode.

The measure of light intensity received at the light intensity detector is a measure indicative of the intensity of light that is received at the light intensity detector. It may be indicative of a ratio of optical power of light received by the light intensity detector to optical power of light emitted from the laser device. For example, it may be the ratio of optical power of light received by the light intensity detector to optical power of light emitted from the laser device, or a ratio of the intensity of light received by the light intensity detector to intensity of light emitted from the laser device, or the percentage transmission of light, or the percentage absorption of light, etc.

Alternatively, the measure of light intensity received may be indicative of the strength of signal received at the detector, for example, the voltage of the signal output from the detector, etc.

The laser absorption spectrometer may further comprise an absorption cell suitable for containing a sample gas, the laser absorption spectrometer being configured such that, in use, laser light emitted from the laser device passes through an absorption cell to the light intensity detector. In use, laser light emitted from the laser device may pass through the absorption cell containing a sample gas to the light intensity detector and the identified extremum may correspond to an absorption peak of the sample gas.

Alternatively, the laser absorption spectrometer may further comprise an etalon and an absorption cell suitable for containing a sample gas, the laser absorption spectrometer being configured such that, in use, laser light emitted from the laser device passes through the etalon, or through the absorption cell, to the light intensity detector. Consequently, the above described method may be performed by passing the light through either the etalon or the sample gas.

The method may further comprise: for each of the plurality of values of the first laser parameter: identifying a plurality of extrema in the measure of light intensity; and identifying for each of the plurality of extrema a respective peak position; wherein the identified range of values of the first laser parameter is a range of values of the first laser parameter within the plurality of values of the first laser parameter for which there is a continuous trend in changes to each peak position in the identified plurality of peak positions with changes to the first laser parameter.

The present disclosure also provides an electronic device configured to perform the above disclosed method.

The present disclosure also provides an electronic device comprising a processor; and a memory storing a software program, wherein the software program, when executed by the processor, causes the processor to perform the above disclosed method.

The electronic device may obtain the measure of light intensity received at the light intensity detector across a range of values of the second laser parameter either by receiving the measure, or by retrieving the measure (for example, from a data store), or by performing the measurements. The electronic device may set the operating value of the first laser parameter to be within the identified range of values of the first laser parameter either by applying the operating value of the first laser parameter to the laser device, or by communicating it to an operator (for example visually, using a screen, or aurally, using a speaker, etc) such that the operator may apply it to the laser device, or by communicating it to a controller on the laser absorption spectrometer (for example, by wired or wireless data transfer), such that the controller may apply it to the laser device.

The present disclosure also provides a laser absorption spectrometer comprising: a laser device for emitting laser light, wherein the wavelength of the laser light is variable by adjusting either of a first laser parameter and a second laser parameter; a light intensity detector configured to measure the intensity of laser light received from the laser device; and either of the above disclosed electronic devices.

The laser absorption spectrometer may further comprise an absorption cell suitable for containing a sample gas, wherein the laser absorption spectrometer is configured such that, in use, laser light emitted from the laser device passes through the absorption cell to the light intensity detector.

The laser absorption spectrometer may further comprise: an etalon; and an absorption cell suitable for containing a sample gas, wherein the laser absorption spectrometer is configured to be set such that, in use, laser light emitted from the laser device passes through the etalon, or through the absorption cell, to the light intensity detector.

The present disclosure also provides a software program configured to perform the above disclosed method when executed on a processor of an electronic device.

It should be noted that any feature described above may be used with any particular aspect of the present disclosure.

BRIEF DESCRIPTION OF THE DRAWINGS

Aspects of the present disclosure shall be described, by way of example only, with reference to the following drawings, in which.

It should be noted that the figures are illustrated for simplicity and are not necessarily drawn to scale. Like features are provided with the same reference numerals.

DETAILED DESCRIPTION OF EMBODIMENTS

It will be appreciated that wavelength of light is inversely proportional to optical frequency of light. Therefore, the terms 'wavelength' and 'optical frequency' in the following are interchangeable. Likewise, the term 'increase in wavelength' (or words to that effect) may be exchanged with 'decrease in optical frequency', and the term 'decrease in wavelength' (or words to that effect) may be exchanged with 'increase in optical frequency'.

Figure 1:
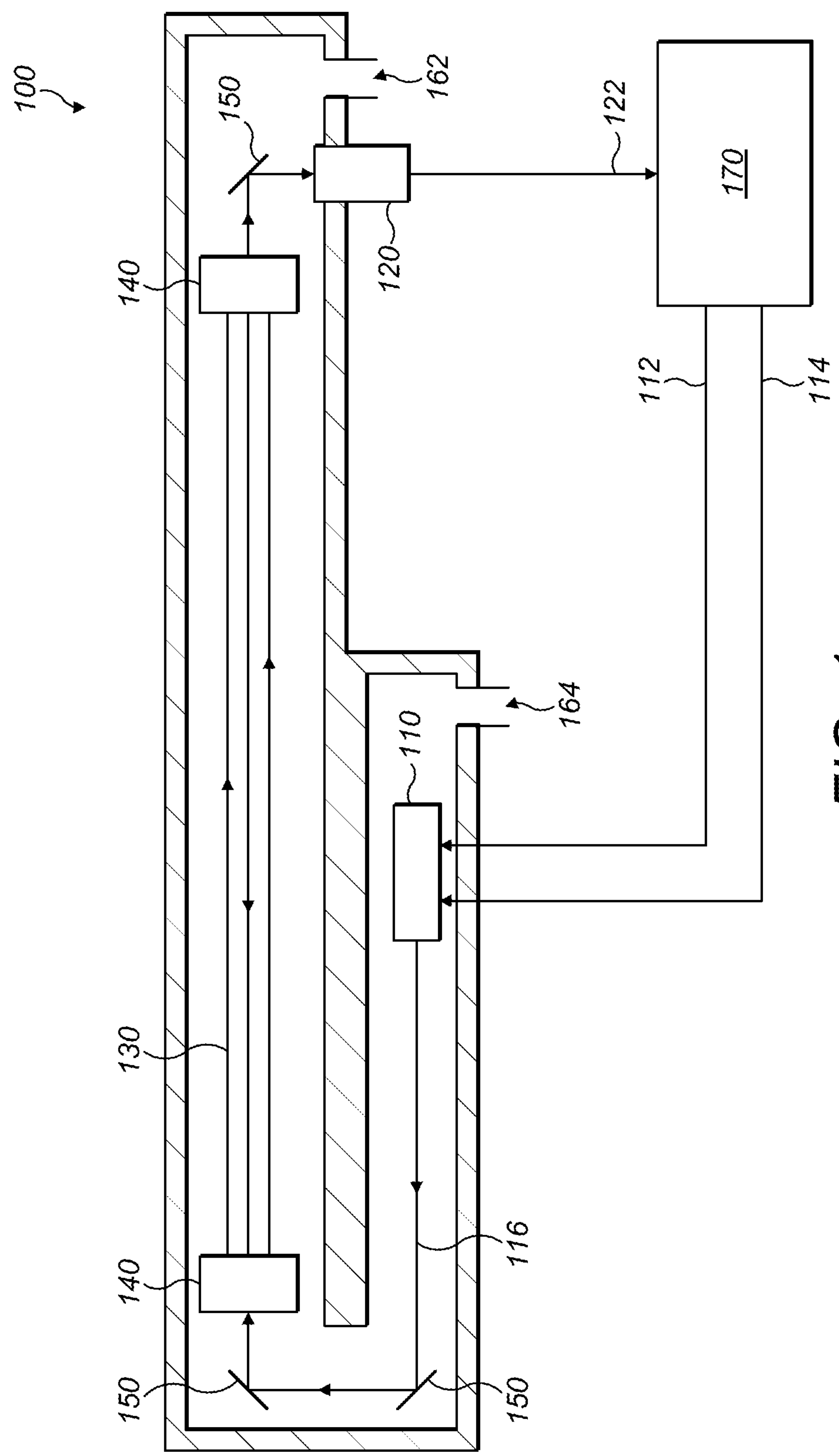
FIG. 1 shows a highly schematic representation of a laser absorption spectrometer 100.

FIG. 1 shows a highly schematic representation of a laser absorption spectrometer 100 in accordance with an aspect of the present disclosure. The laser absorption spectrometer 100 comprises a laser device 110, configured to emit a laser light 116 at a wavelength that is variable by adjusting one or both of a first laser parameter 112 and a second laser parameter 114. The laser absorption spectrometer 100 also comprises a light intensity detector 120, configured to output a measure of light intensity 122 received at the light intensity detector 120, an absorption cell 130 suitable for containing a sample gas, multipass mirrors 140, mirrors 150, sample gas input port 162 and sample gas output port 164. The laser absorption spectrometer 100 also comprises a controller 170, coupled to the laser device 110 and the light intensity detector 120 and configured to obtain the measure of light intensity 122 and control the values of the first laser parameter 112 and the second laser parameter 114.

The laser absorption spectrometer 100 is configured such that a sample gas may be fed into the absorption cell 130 via the sample gas input port 162. The sample gas may be fed into the absorption cell 130 via the gas input port 162, for example through a restriction capillary at a constant flow rate (such as 80 sccm). Optionally, a reference gas may also be fed into the absorption cell 130, either via the gas input port 162 or via a further gas input port (not shown). After passing through the absorption cell 130, the sample gas may be drawn off at the gas output port 164, for example, by a small diaphragm pump and exhausted.

The laser light 116 passes through the gas in the absorption cell 130, making multiple passes between the multipass mirrors 140 in order to increase the path length of the laser light 116 through the sample gas, to the light intensity detector 120. The light intensity detector 120 outputs a measure of light intensity 122 received at the light intensity detector 120, which may be used to identify an isotope ratio and/or concentration in the sample gas (as explained later).

Figure 2:
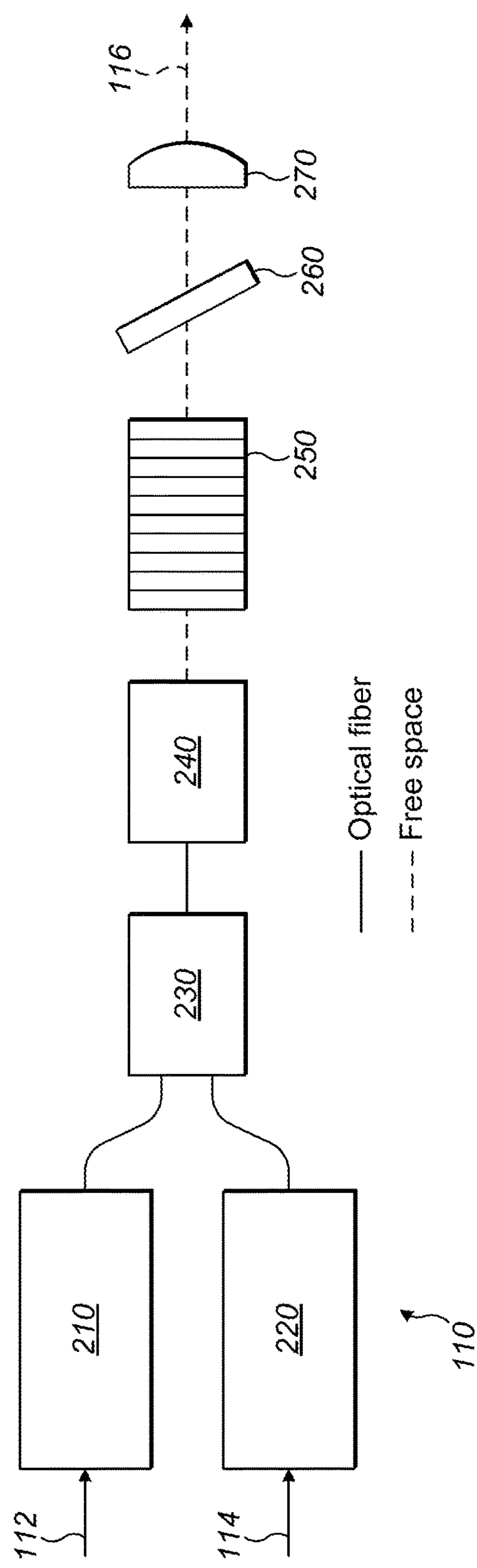
FIG. 2 shows a highly schematic representation of a laser device 110 of the laser absorption spectrometer 100 of FIG. 1.

FIG. 2 shows a highly schematic drawing of the laser device 110 in accordance with an aspect of the present disclosure. The laser device 110 utilises difference frequency generation (DFG) between two telecom laser diodes, and may be of the type described in D. Richter et al., High-precision CO2 isotopologue spectrometer with a different-frequency-generation laser source, Opt. Lett. 34, 172-174 (2009). The laser device 110 comprises a first laser diode 210 and a second laser diode 220, where the wavelength of the first laser diode 210 is smaller than the wavelength of second laser diode 220 (i.e., the optical frequency of the first laser diode 210 is greater than the optical frequency of second laser diode 220). In this example, the first laser diode 210 is a wavelength stabilized (WS) laser diode, and the second laser diode 220 is a distributed feedback (DFB) laser diode. The first laser diode 210 may be wavelength stabilized by a volume holographic grating (VHG) integrated into the packaging of the first laser diode 210 (for example, as described in S. L. Rudder et al., Hybrid ECL/DBR wavelength & spectrum stabilized lasers demonstrate high power & narrow spectral linewidth, Proc. SPIE 6101, 6101oI (2006)). The laser light outputs from the first laser diode 210 and the second laser diode 220 are combined into a single optical fibre by a wavelength division multiplexer (WDM) 230. The combined laser light passes through a fibre focuser 240 into a periodically poled lithium niobate (PPLN) crystal 250 (for example, of the type described at http://www.rp-photonics.com/periodic_poling.html) where light at the difference frequency, which is the difference between the optical frequencies of the laser light of the first laser diode 210 and the second laser diode 220, is generated.

In one example, the first laser diode 210 may generate laser light with a wavelength of 1168 nm and the second laser diode 220 may generate laser light with a wavelength of 1599 nm. The PPLN crystal 250 may be configured to output laser light at a difference frequency corresponding to a wavelength of 4.3 μm. The output laser light then passes through a germanium filter 260 to eliminate the 1599 nm and 1168 nm light and then through a calcium fluoride ($CaF_2$) lens 270.

It will be appreciated that the laser device 110 may alternatively be configured to generate laser light 116 at any desired wavelength in any suitable way. For example, the first laser diode 210 and the second laser diode 220 may be configured to generate laser light at any suitable wavelength in order to generate laser light 116 at any desired wavelength. Additionally, or alternatively, the non-linear crystal 250 may be configured to generate laser light 116 at any desired wavelength, for example by difference frequency generation (DFG) or sum frequency generation (SFG), such that the laser device 110 can be a DFG laser source or a SFG laser source. To this end, the non-linear crystal may be of any suitable material like lithium niobate ($LiNbO_3$), lithium tantalate ($LiTaO_3$), or potassium titanyl phosphate ($KTiOPO_4$) (for example, as described at https://www.rp-photonics.com/nonlinear_crystal_materials.html). Additionally, the non-linear crystal may be periodically poled (PP) to achieve quasi-phase matching, or not. Additionally, the non-linear crystal may have an integrated waveguide structure to increase conversion efficiency, or not (for example, as described at http://www.laserfocusworld.com/articles/print/volume-51/issue-05/features/nonlinear-optics-ppin-waveguides-perform-quantum-frequency-conversion.html). Furthermore, the laser device 110 may optionally not include any one or more of the WDM 230, the fibre focuser 240, the Ge filter 260 and/or the $CaF_2$ lens 270, as necessary. In this particular example, 4.3 μm has been chosen as the wavelength for the laser light 116 as this is a mid-infrared wavelength, which is particularly useful when analysing $CO_2$ because $CO_2$ absorption peaks are particularly strong in the mid-infrared range around this wavelength. Because the absorption peaks are stronger in this range, the laser path length in the absorption cell 130 may be made shorter (typically about 5 m).

The wavelength of laser light 116 may be varied by changing one or both of the first laser parameter 112 and the second laser parameter 114. In the arrangement shown in FIG. 2, the first laser parameter 112 may be the injection current to the first laser diode 210, or the temperature of the first laser diode 210, and the second laser parameter 114 may be the injection current to the second laser diode 220, or the temperature of the second laser diode 220. It will be appreciated that changing at least one of the injection current and/or temperature will change the wavelength of light output from a laser diode.

Thus, if the value of the first laser parameter 112 is changed, the wavelength of the laser light output from the first laser diode 210 will change, and the wavelength of the laser light 116 will correspondingly change. Likewise, if the value of the second laser parameter 114 is changed, the wavelength of the laser light output from the second laser diode 220 will change, and the wavelength of the laser light 116 will correspondingly change.

When performing laser absorption spectrometry (LAS), the wavelength of the laser light 116 is scanned across the absorption peaks of a species (or isotopologue) in the sample gas. Typically, in the embodiment shown, this is achieved by varying the wavelength of laser light emitted from the second laser diode 220, while keeping the wavelength of laser light emitted from the first laser diode 210 constant. In other arrangements, the laser diode that is kept at constant wavelength and the laser diode that is varied may be interchanged. In still further arrangements, the wavelength of light emitted from both laser diodes may be varied.

Figure 3:
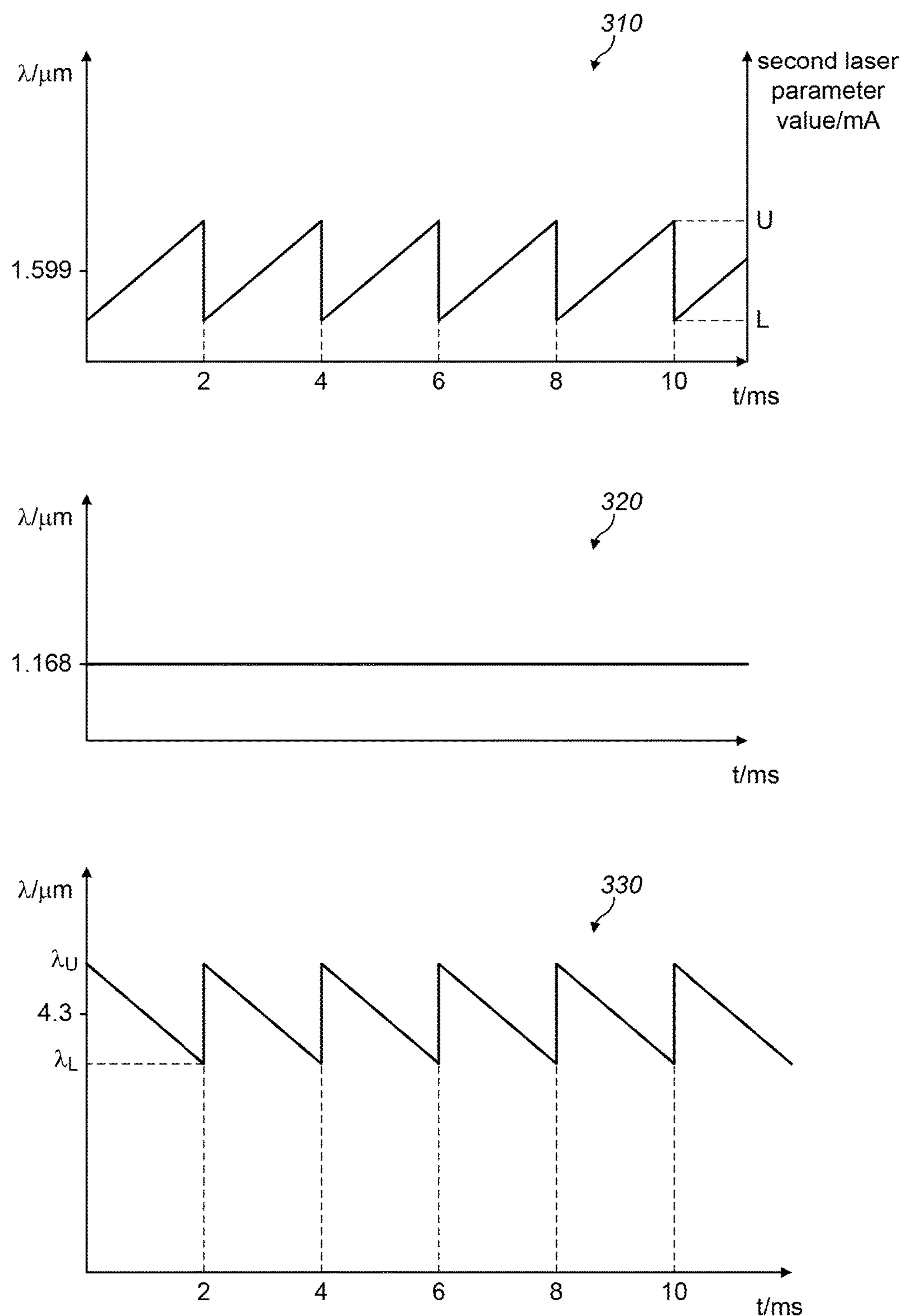
FIG. 3 shows an example plot of the wavelength of light emitted from the laser device 110 of FIG. 2.

FIG. 3 shows an example plot of the wavelength of light emitted from the first laser diode 210, the wavelength of light emitted from the second laser diode 220 and the wavelength of laser light 116. Plot 310 represents the wavelength of light emitted from the second laser diode 220. A ramped injection current (in this example a saw-tooth waveform with an upward current ramp) is applied to the second laser diode 220 as the second laser parameter 114 while the temperature of the second laser diode 220 is held constant. The ramped injection current is continuously scanned over a range from a lower value, L, to an upper value, U. This generates a corresponding ramped wavelength of laser light emitted from the second laser diode 220, such that the wavelength of laser light emitted from the second laser diode 220 is continuously scanned over an optical wavelength range. In an alternative, a ramped laser diode temperature may be applied as the second laser parameter 114 with the injection current to the second laser diode 220 held constant in order to generate the ramped wavelength of laser light emitted from the second laser diode 220.

In this example, the wavelength of laser light emitted from the second laser diode 220 is centred at 1599 nm and the optical wavelength range corresponds to an optical frequency range of 30 GHz, although it will be appreciated that the laser light may be centred at any suitable wavelength with any suitable optical wavelength range. The scan repetition rate in this example is 500 Hz (a time period of 2 ms), although it will be appreciated that the scan repetition rate may be any suitable rate.

Plot 320 in FIG. 3 represents the wavelength of light emitted from the first laser diode 210. The first laser diode 210 is held at a constant temperature and constant injection current, and so emits laser light at a constant wavelength. In this example, the wavelength of laser light emitted from the first laser diode 210 is 1168 nm, although it will be appreciated that the laser light may be at any suitable wavelength.

Plot 330 in FIG. 3 represents the wavelength of laser light 116. As a result of the ramped wavelength of laser light emitted from the second laser diode 220, the wavelength of laser light 116 is also ramped. However, because the laser device 110 is a DFG laser, and the frequency of the laser light emitted from the second laser diode 220 is subtracted from the frequency of the laser light emitted from the first laser diode 210, as the wavelength of the laser light emitted from the second laser diode 220 is ramped up, the wavelength of laser light 116 is ramped in the opposite way. This may be readily appreciated from the below formula, where $\nu$ is the optical frequency of the laser light 116, $\nu_1$ is the optical frequency of laser light emitted from the first laser diode 210, $\nu_2$ is the optical frequency of laser light emitted from the second laser diode 220, $\lambda$ is the wavelength of the laser light 116, $\lambda_1$ is the wavelength of laser light emitted from the first laser diode 210, $\lambda_2$ is the wavelength of laser light emitted from the second laser diode 220.

$$\nu=\nu_1-\nu_2$$

$$\lambda=1/((1/\lambda_1)-(1/\lambda_2))$$

Therefore, the wavelength of laser light 116 is continuously scanned over a wavelength range, between an upper wavelength limit $\lambda_U$ and a lower wavelength limit $\lambda_L$. The wavelength of laser light 116 is centred on 4.3 μm with a wavelength range corresponding to an optical frequency range of 30 GHz. The scan repetition rate is 500 Hz. Changes to the wavelength range and/or repetition rate of the laser light 116 may be effected by changing the waveform of the wavelength of the laser light from the second laser diode 220.

Figure 4:
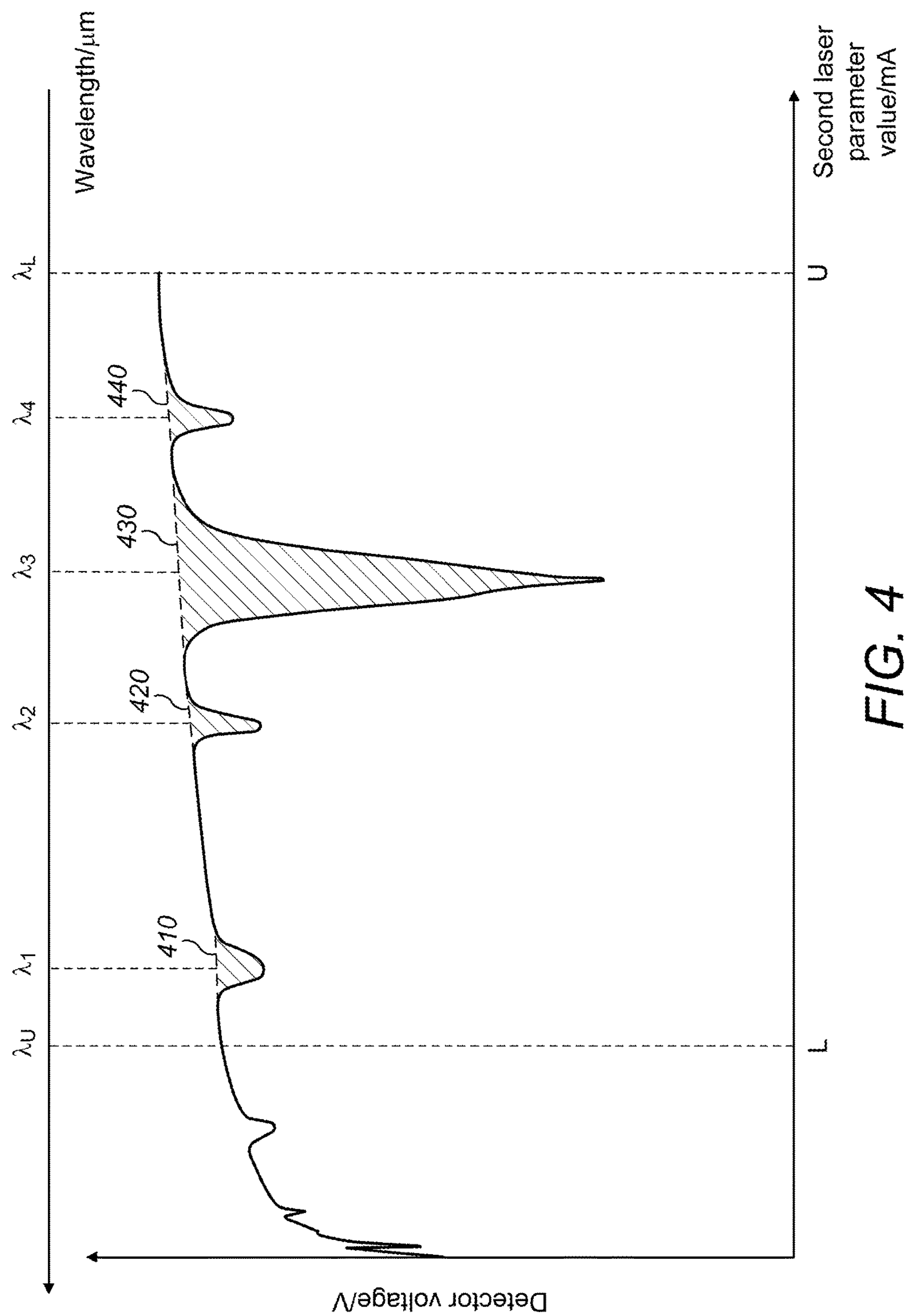
FIG. 4 shows an example gas spectrum obtained by the laser absorption spectrometer 100 of FIG. 1.

FIG. 4 shows an example plot of absorption peaks of three $CO_2$ isotopologues from a sample of $CO_2$ in the absorption cell 130. The gas pressure and temperature in the absorption cell 130 may be controlled and kept constant at 100 mbar and 37.5 C respectively. The wavelength of the laser light 116 is scanned over a wavelength range between the upper wavelength limit $\lambda_U$ and the lower wavelength limit $\lambda_L$ by ramping the second laser parameter value from the lower value L to the upper value U. The measure of light intensity 122 (in this instance, the detector voltage output from the detector 120) is taken across the wavelength range between $\lambda_U$ and $\lambda_L$. The plot of measured light intensity 122 (detector voltage) verses wavelength represented in FIG. 4 shows reductions in measured light intensity 122 at particular wavelengths. These reductions are often referred to as absorption peaks and are caused by particular $CO_2$ isotopologues absorbing the laser light 116 at those particular wavelengths due to quantum mechanical rotational-vibrational states.

Each of these reductions in measured light intensity 122 may be identified as extrema in the spectrum using a peak-find algorithm, which takes the first differential of the measured light intensity 122 to identify extrema (minima or maxima) in the measured light intensity plot. Other peak-find algorithms may be used. In this example, the extrema in the spectrum are light transmission minima, but they could alternatively be represented by light absorption maxima. The peak-find algorithm may provide a first guess of the peak positions (and optionally also the peak areas), which may then serve as a starting point for a peak-fitting algorithm to fit a mathematical function (which may be based on a number of Voigt profiles) to the measured light intensity plot. The process of scanning the laser light wavelength, running the peak-find algorithm and the peak-fitting algorithm may be performed by the controller 170.

In the example plot represented in FIG. 4, the first absorption peak 410 may be identified as taking place at a wavelength $\lambda_1$, which indicates that the first absorption peak 410 is caused by the isotopologue $^{12}C^{18}O^{16}O$. The second absorption peak 420 may be identified as taking place at a wavelength $\lambda_2$, which indicates that the second absorption peak 420 is caused by the isotopologue $^{13}C^{16}O^{16}O$. The third absorption peak 430 may be identified as taking place at a wavelength $\lambda_3$, which indicates that the third absorption peak 430 is caused by the (major) isotopologue $^{12}C^{16}O^{16}O$. The fourth absorption peak 440 may be identified as taking place at a wavelength $\lambda_4$, which indicates that the fourth absorption peak 440 is caused by the (major) isotopologue $^{12}C^{16}O^{16}O$.

The peak strength of each of the absorption peaks may also be identified. The peak strength may be the peak area, which is the area of the hatched region of each of the absorption peaks 410, 420, 430 and 440, as shown on the plot represented in FIG. 4. As part of the determination of peak strength, the peak-fitting algorithm may also determine the baseline, which is the detector voltage in the case where there was no absorption from the sample gas. The baseline value is represented in FIG. 4 by the dashed lines that continue the trend of the detector voltage lines between the absorption peaks and close the top of the peak areas. The ratio and/or concentration of each of the identified isotopologues may be determined from the peak strengths associated with each isotopologue. To this end, a peak-fitting algorithm may be used to fit a mathematical function, which may be based on a number of Voigt profiles, to the measured light intensity 122. By this, the peak strengths can be determined with sufficient accuracy as required by isotope ratio measurements. Alternatively, the peak strength of each absorption peak may be the peak height, which is the percentage absorption (as described below) at the identified peak position of each absorption peak 410, 420, 430 and 440. Alternatively, the peak strength of each absorption peak may be a value derived from at least one of the peak area and/or the peak height. Consequently, the concentrations of the three main $CO_2$ isotopologues and the resulting $^{13}C$:$^{12}C$ and $^{18}O$:$^{16}O$ isotope ratios may be calculated from the peak strengths, which may be obtained by use of a peak-fitting algorithm. The baseline may be part of the output of the peak-find or peak-fitting algorithm.

As explained in the 'background' section, in order accurately to identify each of the isotopologues using the above described process, it is preferable for the laser light 116 to be of single-frequency at any particular moment as it is being scanned across the wavelength range. Furthermore, it is also desirable that as the wavelength of the laser light 116 is varied across the absorption peaks, the wavelength is tuned (i.e., increased or decreased) continuously and predictably.

For DFB type laser diodes, these requirements are not normally a problem. Therefore, meeting these requirements should not normally be an issue for the second laser diode 220. However, for WS type laser diodes, these requirements may be difficult as they are prone to multimoding and/or mode hopping if the laser temperature and/or current is not set correctly. Multimoding might cause the spectrum of the measured light intensity 122 to become distorted and split, thereby spoiling the isotope ratio and concentration measurement results. Mode hoping might cause sudden jumps in the wavelength of the laser light 116, causing the absorption peaks to abruptly shift, thereby spoiling the isotope ratio and concentration measurement results.

During primary configuration of the laser absorption spectrometer 100, a stable operating point may be set for the first laser diode 210 using an optical spectrum analyser, as explained in the 'background' section. An example operating point is found to be an operating temperature of the first laser diode 210 of 25° C. and an operating value of the first laser parameter of 400 mA. An operating value of 400 mA for the first laser parameter 112 might put the first laser diode 210 in the centre of a stable operating region that is at least 40 mA wide (i.e., if the first laser parameter 112 were to increase or decrease by up to 20 mA, the laser light 116 should still be of a single-frequency without mode-hopping, but if it were to increase or decrease by more than that, the light emitted from the first laser 210, and therefore the laser light 116, might encounter multimoding and/or mode hopping). For the WS laser diode used in this example, a width of 40 mA has proven to be feasible for most laser diodes and ensure stable operation of the laser diode. It will be appreciated that the minimum size of the stable operating region may be set to any suitable value, for example, at least 20 mA, at least 30 mA, at least 55 mA, etc. However, as also explained in the 'background' section, the centres and widths of stable regions may vary as the first laser diode 210 ages, which might cause a previously stable operating point of the first laser diode 210 to move into an unstable region.

The present disclosure provides a technique for re-optimizing the operating value of the first laser parameter 112 (which could be either the injection current or temperature of the first laser diode 210) that utilises the peak-find algorithm described above.

Figure 5:
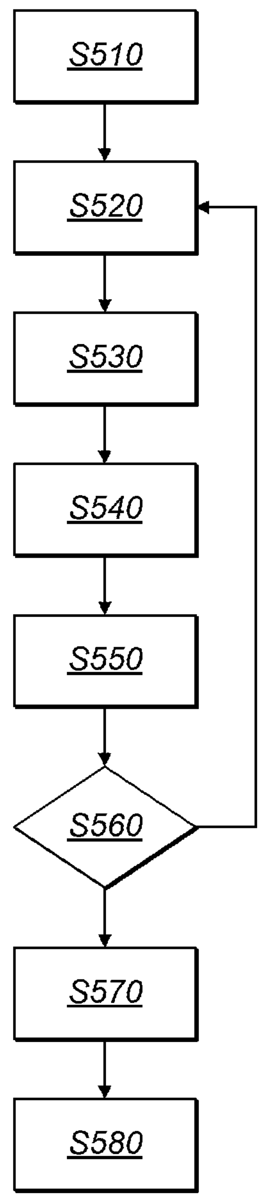
FIG. 5 shows a flow chart representing the steps of a method for optimizing an operating value of a laser parameter of the laser device of FIG. 2.

FIG. 5 shows a flowchart representing the steps of a method for optimizing an operating value of the first laser parameter 112 of the laser device 110 in accordance with an aspect of the present disclosure. The process steps may be performed by the controller 170. The controller 170 may comprise a computer or electronic device including a processor and memory storing a software program, wherein the software program, when executed by the processor, causes the processor and thus the controller 170, to perform the method described.

In Step S510, the first laser parameter 112 is set to an initial value. In this example, the first laser parameter is the injection current to the first laser diode 210. An example initial value is 340 mA, which may be set in view of the operating value of the first laser parameter 112 having been set to 400 mA during primary configuration. It will be appreciated that the initial value may be any suitable current value, for example 10 mA, or 50 mA, or 100 mA, or 200 mA, or 380 mA, or 500 mA, or 800 mA, or 1.2 A, etc.

In Step S520, a measure of light intensity 116 is obtained across a range of values of the second laser parameter 114. The light intensity is measured by performing the process described in respect of FIGS. 3 and 4 above. In particular, a ramped injection current is applied to the second laser diode 220 as the second laser parameter 114, such that the wavelength of the laser light 116 decreases across a continuous range of wavelengths from an upper wavelength limit $\lambda_U$ to a lower wavelength limit $\lambda_L$. The range of wavelengths between the lower wavelength limit $\lambda_L$ and the upper wavelength limit $\lambda_U$ may be considered as the spectral window of the laser absorption spectrometer 100.

Figure 6:
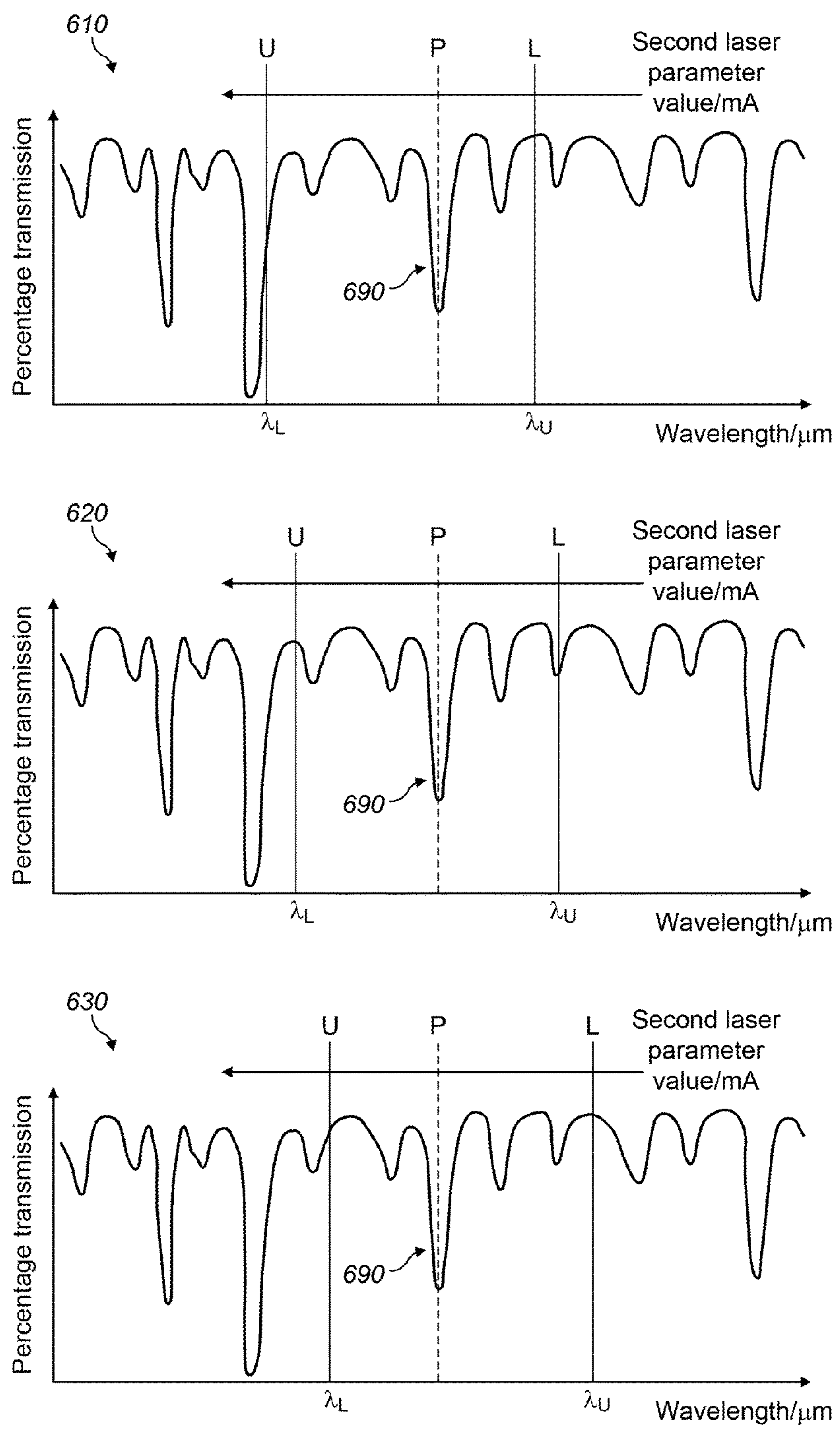
FIG. 6 shows a representation of a measure of light intensity received at the light intensity detector of the laser absorption spectrometer of FIG. 1 during the method of FIG. 5.

FIG. 6 shows a representation of the measure of light intensity 122 during the process of re-optimization. Plot 610 represents the measure of light intensity 122 when the first laser parameter 112 is set to the initial value. The measure of light intensity 122 in this example is the percentage transmission, which is indicative of a ratio of optical power of light received at the light intensity detector 120 to the optical power of light transmitted from the laser device 110. In particular, it may be calculated using the signal at the detector 120 and the baseline determined by the peak-find algorithm as described above. In particular, the percentage transmission may be calculated as follows:

transmission=detector signal/baseline percentage transmission=(detector signal/baseline)×100

Thus, where there is no absorption from the sample gas, the percentage transmission should be 100% (or very close to 100%), and where there is complete absorption from the same case, the percentage transmission should be 0% (or very close to 0%).

In an alternative, the measure of light intensity 122 may be percentage absorption, which may be calculated as follows:

percentage absorption=(1−transmission)×100

The spectral window is represented in plot 610 by the lower wavelength limit $\lambda_L$ and the upper wavelength limit $\lambda_U$, and the corresponding upper value U and lower value L of the second laser parameter 114. While parts of the spectrum outside the spectral window are included in the plot 610, this is merely so that the entire spectrum of the sample gas can be visualised. The measure of light intensity 122 across the range of values of the second laser parameter 114 (i.e., across the ramp of injection current to the second laser diode 220) will be those parts of the spectrum within the spectral window.

In step S530, at least one extremum in the measure of light intensity 122 (percentage transmission) is found. In the example plot 610, only one extremum 690 (a minimum) is identified and may be found using the peak-find algorithm described earlier. It will be appreciated that only one extremum may be identified, for example because there is only one extremum in the measure of light intensity 122 in the spectral window or because the process is set up to find only one extremum (for example, the first extremum in the spectral window, or the largest extremum in the spectral window, etc). Alternatively, two or more extrema in the spectral window may be identified. The example plot 610 shows only one identified extremum 690 for the sake of clarity.

In step S540, the peak position of the identified extremum 690 is identified. In this example, the peak position of the identified extremum 690 is the value P of the second laser parameter 114 at the identified extremum 690. In particular, this is the value of the second laser parameter 114 being scanned from a lower value L to an upper value U at which the identified extremum 690 is identified. The peak position of the identified extremum 690 may additionally or alternatively be the relative wavelength of the laser light 116 at the identified extremum 690 relative to a reference wavelength (for example, the upper wavelength limit $\lambda_U$) in the range of wavelengths across which the laser light 116 is scanned by the range of values of the second laser parameter 114 (i.e., the spectral window of the laser light 116 from $\lambda_L$ to $\lambda_U$).

In step S550, the value of the first laser parameter 112 is increased by a predetermined amount. In this example, it is increased by 0.3 mA, although it will be appreciated that it may be increased by any suitable amount, for example, 0.1 mA, 0.25 mA, 0.4 mA, 1 mA, 1.8 mA, 3 mA, etc, etc. As will be apparent from the following description, the smaller the increment, the finer the measurements will be, but the longer the re-optimization process will be.

Figure 11:
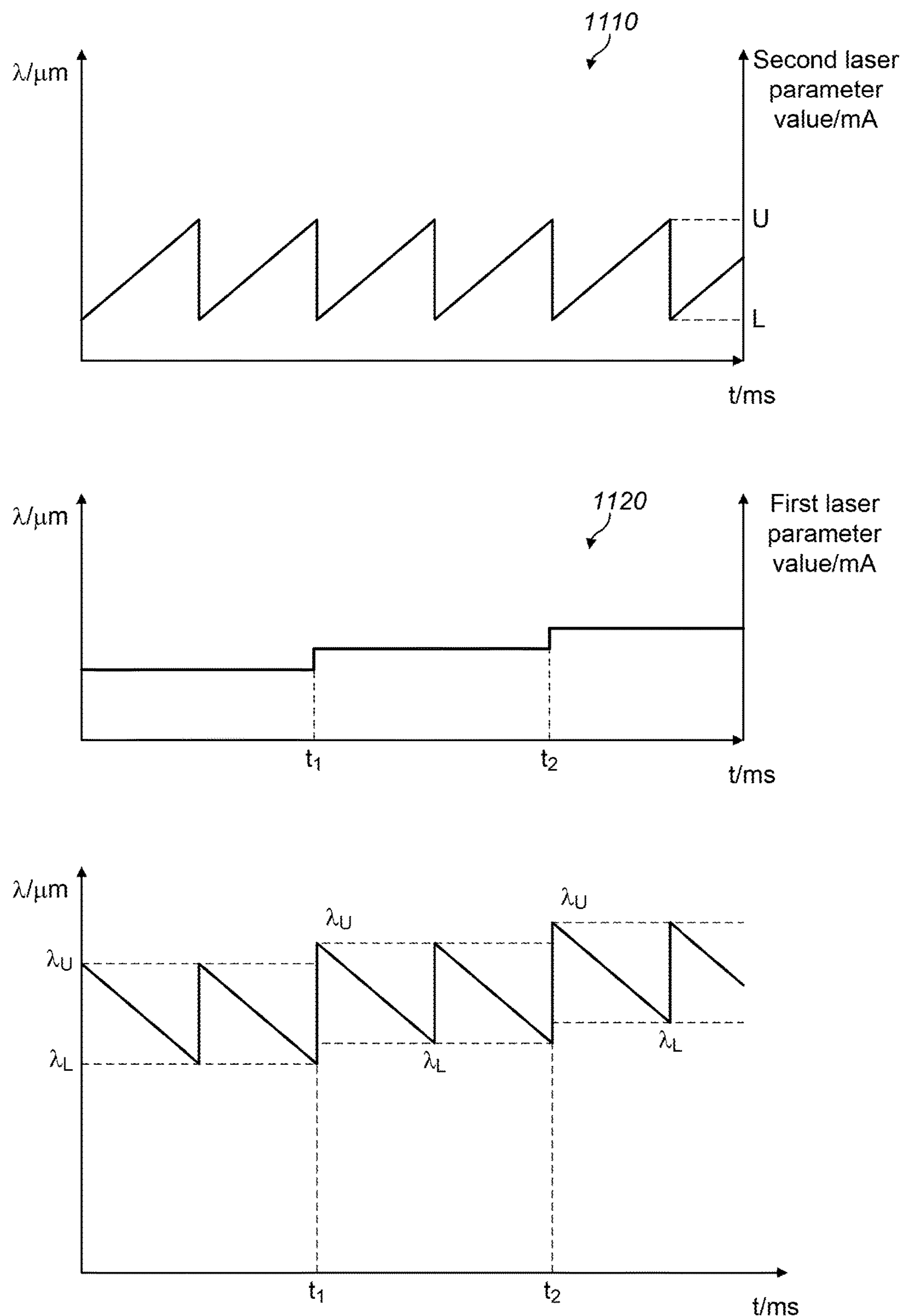
FIG. 11 shows an example plot of the wavelength of light emitted from the laser device 110 during the method of FIG. 5.

FIG. 11 shows an example plot of the wavelength of light emitted from the first laser diode 210, the wavelength of light emitted from the second laser diode 220 and the wavelength of laser light 116. The plots demonstrate the effect on the wavelength of the laser light 116 caused by increasing the value of the first parameter 112. Plot 1110 represents the wavelength of light emitted from the second laser diode 220 and is very similar to plot 310 in FIG. 3. The ramped injection current is continuously scanned over a range from a lower value, L, to an upper value, U.

Plot 1120 in FIG. 11 represents the wavelength of light emitted from the first laser diode 210. It is similar to plot 320 in FIG. 3, but at time $t_1$, the value of the first laser parameter 112 is increased (in step S550, as described above). At time $t_2$, the value of the first laser parameter 112 is further increased (when the process returns again to step S550, as described above and below).

Plot 1130 in FIG. 11 represents the wavelength of laser light 116. It is similar to plot 330 in FIG. 3, but shows that at time $t_1$, the upper wavelength limit $\lambda_U$ and lower wavelength limit $\lambda_L$ both increase, as a consequence of the increase in the wavelength of light emitted from the first laser diode 210 (because the laser device 110 is a DFG type laser, wherein the frequency of the laser light emitted from the second laser diode 220 is subtracted from the frequency of the laser light emitted from the first laser diode 210). At time $t_2$, the upper wavelength limit $\lambda_U$ and lower wavelength limit $\lambda_L$ again both increase further, as a consequence of the increase in the wavelength of light emitted from the first laser diode 210.

While FIG. 11 shows that the second laser parameter value is ramped over a range from a lower value, L, to an upper value, U twice for each value of the first laser parameter 112, it will be appreciated that the second laser parameter value may be ramped over a range from a lower value, L, to an upper value, U any number of times for each value of the first laser parameter 112. For example, it may be ramped over a range from a lower value, L, to an upper value, U only once for each value of the first laser parameter 112, or a plurality of times, such as 20 times, or 100 times, or 500 times, or 1000 times, etc. For example, for each value of the first laser parameter 112, the second laser parameter value may be ramped over a range from a lower value, L, to an upper value, U between 10 and 1000 times, or between 100 and 1000 times, or between 300 and 800 times. In a preferred configuration, the second laser parameter value is ramped over a range from a lower value, L, to an upper value, U approximately 500 times (for example, between 490 and 510 times) for each value of the first laser parameter 112. A spectrum is obtained for each ramp and the spectra are averaged to create a single spectrum with good signal-to-noise ratio for each value of the first laser parameter. The averaged spectrum for each value of the first laser parameter is shown in each of plots 610, 620 and 630 of FIG. 6.

In step S560, it is determined whether or not an upper limit of the first laser parameter 112 has been reached. In this example, the upper limit of the first laser parameter 112 is set to 460 mA, although it may be set to any suitable value such that the re-optimization process is carried out across a suitable range of values of the first laser parameter 112. If it is determined that the value of the first laser parameter 112 is less than or equal to the upper limit, the process returns to step S520. If it is determined that the value of first laser parameter 112 is greater than the upper limit, the process proceeds to S570 (which is described in more detail later).

After returning to step S520, each of steps S520, S530 and S540 are repeated again. Plot 620 in FIG. 6 shows a representation of the measure of light intensity 122 and the peak position P of the identified extremum for the incremented value of the first laser parameter 112. As can be seen, the absorption spectrum of the sample gas is the same as plot 610 and has the same extrema occurring at the same wavelengths of laser light 116 as in plot 610. This is because the sample gas is unchanged and so will consistently absorb laser light 116 at the same wavelengths of laser light. The range of values of the second laser parameter 114 from the lower value L to the upper value U is the same as the range of values used previously for plot 610, but because the value of the first laser parameter 112 has increased, the spectral window has shifted (i.e., the wavelengths of laser light 116 have increased for each value of the second laser parameter 114 by virtue of the increase in the value of the first laser parameter 112). This can be seen by $\lambda_L$ in plot 620 being at a greater wavelength than $\lambda_L$ in plot 610, and $\lambda_U$ in plot 620 being at a greater wavelength than $\lambda_U$ in plot 610. Because the absolute wavelength of light of the identified extremum 690 stays the same, the peak position P of the identified extremum 690 in plot 620 is greater than in plot 610 (i.e., the value of the second laser parameter 114 at which the extremum 690 is identified is greater in plot 620 than in plot 610).

Having identified the peak position P of the extremum 690 in step S540, the process again proceeds to step S550 where the value of the first laser parameter 112 is further increased. If it is determined in step S560 that the value of the first laser parameter 112 is still less than or equal to the upper limit, the process will again return to step S520.

Plot 630 in FIG. 6 shows a representation of the measure of light intensity 122 and the peak position P of the identified extremum 690 for the further incremented value of the first laser parameter 112. It can be seen that again the spectral window has shifted and the peak position P of the identified extremum 690 has further increased.

This process is repeated until it is determined in step S560 that the value of the first laser parameter 112 is greater than the upper limit, at which time the process will proceed to step S570. By now, the peak position of the identified extremum will have been identified for each of the plurality of values of the first laser parameter 112. Thus, there will be a data set comprising the plurality of values of the first laser parameter 112 and the corresponding peak position P of the identified extremum 690 for each of the values of the first laser parameter 112.

In step S570, a range of values of the first laser parameter 112 within the plurality of values of the first laser parameter 112 for which there is a continuous trend in changes to the identified peak positions P with changes to the first laser parameter 112 is identified.

Figure 7:
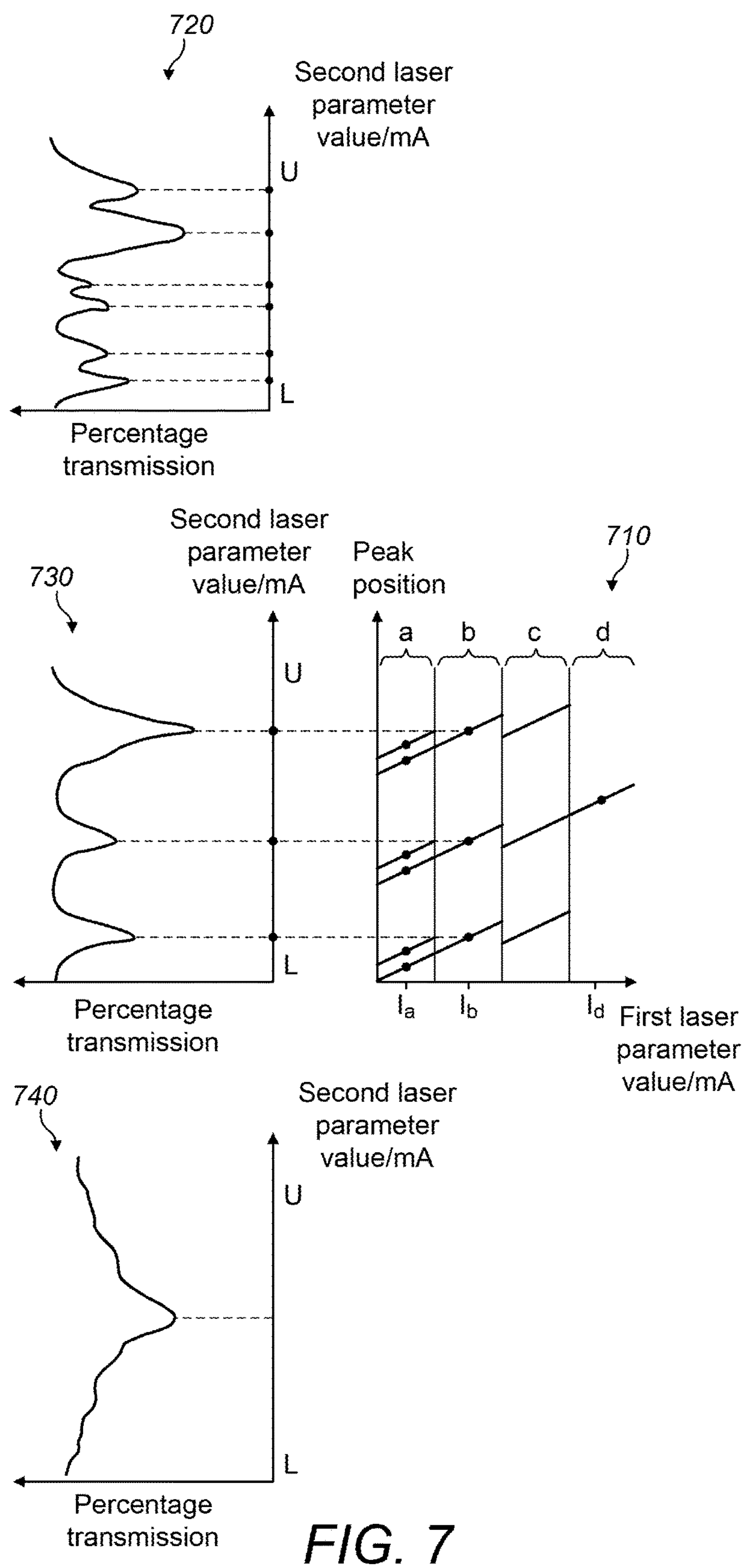
FIG. 7 shows a graphical representation of changes to the identified peak positions with changes to the first laser parameter during the method of FIG. 5.

FIG. 7 shows a graphical representation of changes to the identified peak positions with changes to the first laser parameter 112. Plot 710 in FIG. 7 shows a plot of the identified peak position against the first laser parameter value 112, represented here by the corresponding value of the second laser parameter 114. For each value to which the first laser parameter 112 is set, the corresponding peak position for each identified extrema is plotted. It can be seen that as the value of the first laser parameter 112 increases, the peak position of each identified extrema generally increases. Four regions of the plot are marked—regions a, b, c and d.

Plot 720 shows an example spectrum of the measured of light intensity 122 within the spectral window defined by the lower wavelength limit $\lambda_L$ and the upper wavelength limit $\lambda_U$. The first laser parameter 112 is at a particular value (i.e., the injection current to the first laser diode 210 is $I_a$), and the peak find algorithm has identified six extrema, each represented by a dot on the second laser parameter value axis of the plot. A corresponding set of six dots is identified within region ‘a’ of plot 710.

Plot 730 shows another example spectrum of the measured of light intensity 122 within the spectral window defined by the lower wavelength limit $\lambda_L$ and the upper wavelength limit $\lambda_U$. The first laser parameter 112 is at a different value to that of plot 720, (i.e., the injection current to the first laser diode 210 is $I_b$, where $I_b$ is greater than $I_a$), and the peak-find algorithm has identified three extrema, each represented by a dot on the second laser parameter value axis of the plot. A corresponding set of three dots is identified within region ‘b’ of plot 710.

Plot 740 shows another example spectrum of the measured of light intensity 122 within the spectral window defined by the lower wavelength limit $\lambda_L$ and the upper wavelength limit $\lambda_U$. The first laser parameter 112 is at a different value to that of plots 720 and 730, (i.e., the injection current to the first laser diode 210 is $I_d$, where $I_d$ is greater than $I_b$), and the peak-find algorithm has identified one extremum, represented by a dot on the second laser parameter value axis of the plot. A corresponding dot is identified within region ‘d’ on plot 710.

It can be seen that within region ‘b’ and within region ‘c’ in plot 710, there is a continuous trend in changes to the identified peak positions with changes to the first laser parameter 112. A continuous trend may be one that can be defined by a continuous function (for example, a function for which small changes in the input (the first laser parameter 112) result in small changes in the output (peak position)). In this example, it is a continuous linear trend, or near-linear trend, although the trend does not necessarily have to be linear.

A continuous trend indicates that the wavelength of light from the first laser diode 210 (and therefore wavelength of the laser light 116) is changing continuously and predictably. At the interface between regions ‘b’ and ‘c’, there is a discontinuity in the peak position, as can be seen by the sudden drop in peak position (a vertical offset). This indicates a mode hop in the laser diode 210, which causes the wavelength of light no longer to change continuously and predictably. In other words, for a range of values of the first laser parameter that is taken from the middle of region ‘b’ to the middle of region ‘c’, there is not a continuous trend in changes to the identified peak position due to discontinuity in the peak position.

Therefore, it can be seen that by identifying in step S570 a range of values of the first laser parameter 112 for which there is a continuous trend in changes to the identified peak positions with changes to the first laser parameter 112, a stable region of operation of the first laser diode 210 is identified (for example, region ‘b’ or region ‘c’).

In step S580, the operating value of the first laser parameter 112 is set to be within the identified range of values of the first laser parameter 112. Preferably the operating value is set to be in the centre of the range, or to within a threshold tolerance of the centre of the range (for example, within ±1%, ±2%, ±5%, ±10%, ±0.01 mA, ±0.03 mA, ±0.1 mA, ±0.5 mA, etc, etc). The operating value may alternatively be set to any value that is closer to the middle of the identified range that it is to either end of the identified range.

By setting the operating value of the first laser parameter 112 to be at, or close to, the centre of the identified range, the first laser diode 210 will operate stably, such that there is no mode-hopping in the laser light output from the first laser diode 210. As a consequence, when the laser absorption spectrometer 100 is being used to analyse a sample gas in the future, the wavelength of the laser light 116 should scan continuously and predictably across the absorption peaks of the sample gas, because the first laser diode 210 should output a stable laser light without any mode-hopping.

In the present example, regions ‘b’ and c' may both be identified as regions for which there is a continuous trend in changes to the identified peak position with changes to the first laser parameter 112. In this case, in step S580, the operating value may be set to a value within the largest of the identified ranges (the largest range being the range with the greatest difference between the maximum value within the range and the minimum value within the range). By setting the operating value of the first laser parameter 112 in this way, the laser diode 210 may operate in the most-stable region, thereby minimising the possibility that it will start to operate unstably in the future.

While mode-hopping of the first laser diode 210 has been taken into consideration and avoided by setting the operating value of the first laser parameter 112 as described above, multimoding of the first laser diode 210 has not been accounted for. In order to ensure that the operating value of the first laser parameter 112 is set in a region in which both mode-hopping and multimoding are avoided, further analysis may be done as part of at least some of the steps of the process described above.

In a first aspect, in step S570, it may also be determined whether or not the number of identified extrema corresponds with an expected number of extrema for the sample gas in the absorption cell 130. For example, the sample gas may be $CO_2$ and it may be expected that only three extrema should be identified, for example within a particular spectral window. In this instance, in region 'a', the laser diode 210 is multimoding, which is causing peak splitting in the spectrum (six (artefact) peaks being identified instead of three (real) peaks). Therefore, there are too many extrema in the spectrum within region 'a'. Likewise, in region 'd', again the laser diode 210 is multimoding, which is causing the spectra shape to be heavily distorted such that only one extrema is identified by the peak-find algorithm.

Therefore, by determining a range of values of the first parameter 112 for which: there is a continuous trend in changes to the identified peak positions with changes to the first laser parameter 112; and the number of identified extrema at each of the plurality of values of the first laser parameter 112 corresponds with an expected number of extrema, both mode hoping and multimoding may be avoided. In the present example, only regions 'b' and 'c' would be identified as suitable ranges of values of the first parameter 112, and the operating value of the first parameter 112 may be set to a value that is in the larger of regions 'b' and 'c'. In an alternative example, only a single suitable range may be identified, in which case the operating value of the first laser parameter 112 may be set to a value in that single range, or three or more suitable ranges may be identified, in which case the operating value of the first laser parameter 112 may be set to a value in the largest of the identified ranges.

While the above technique may help to avoid regions of multimoding, it requires knowledge of how many extrema should be identified for the sample gas. This may require an exact knowledge of the size and position of the spectral window on the wavelength axis in order to determine the expected number of extrema. However, it will be appreciated that in some scenarios, this may be inconvenient. In an alternative, a comparison may be made between at least some of the absorption spectra obtained during the above described process and a theoretical spectrum of the sample gas (preferably for each value of the first laser parameter 112, to ensure that a correct determination of multimoding is made for each value of the first laser parameter 112) to determine if the number of identified extrema is correct for the sample gas.

In a further alternative, in order to identify regions of multimoding, a measure of absorption strength of laser light for each of the identified extrema may be considered. One example of absorption strength of laser light is the peak strength of each identified extrema. As explained earlier, the peak strength can be given by the area of the extrema absorption on the spectrum plot (as shown in FIG. 4). If the measure of light intensity 122 is the percentage transmission plotted against the second laser parameter value (in this instance, the injection current), the unit of peak area will be mA (because percentages are unitless). However, it will be appreciated that the unit of peak area may be any other suitable unit, for example V.mA, where the measure of light intensity 122 is the voltage output from the light intensity detector 120.

In step S530, in addition to identifying at least one extremum in the measure of light intensity 122, the peak strength of each of the identified extrema may also be identified. Alternatively, the peak strength of each of the identified extrema may be identified in step S540, in addition to identifying the peak position (given by the corresponding value of the second laser parameter 114) of each identified extremum.

In step S570, in addition to considering how the identified peak positions change with changes to the value of the first laser parameter 112, how the identified peak strengths change with changes to the value of the first laser parameter 112 is also considered.

Figure 8:
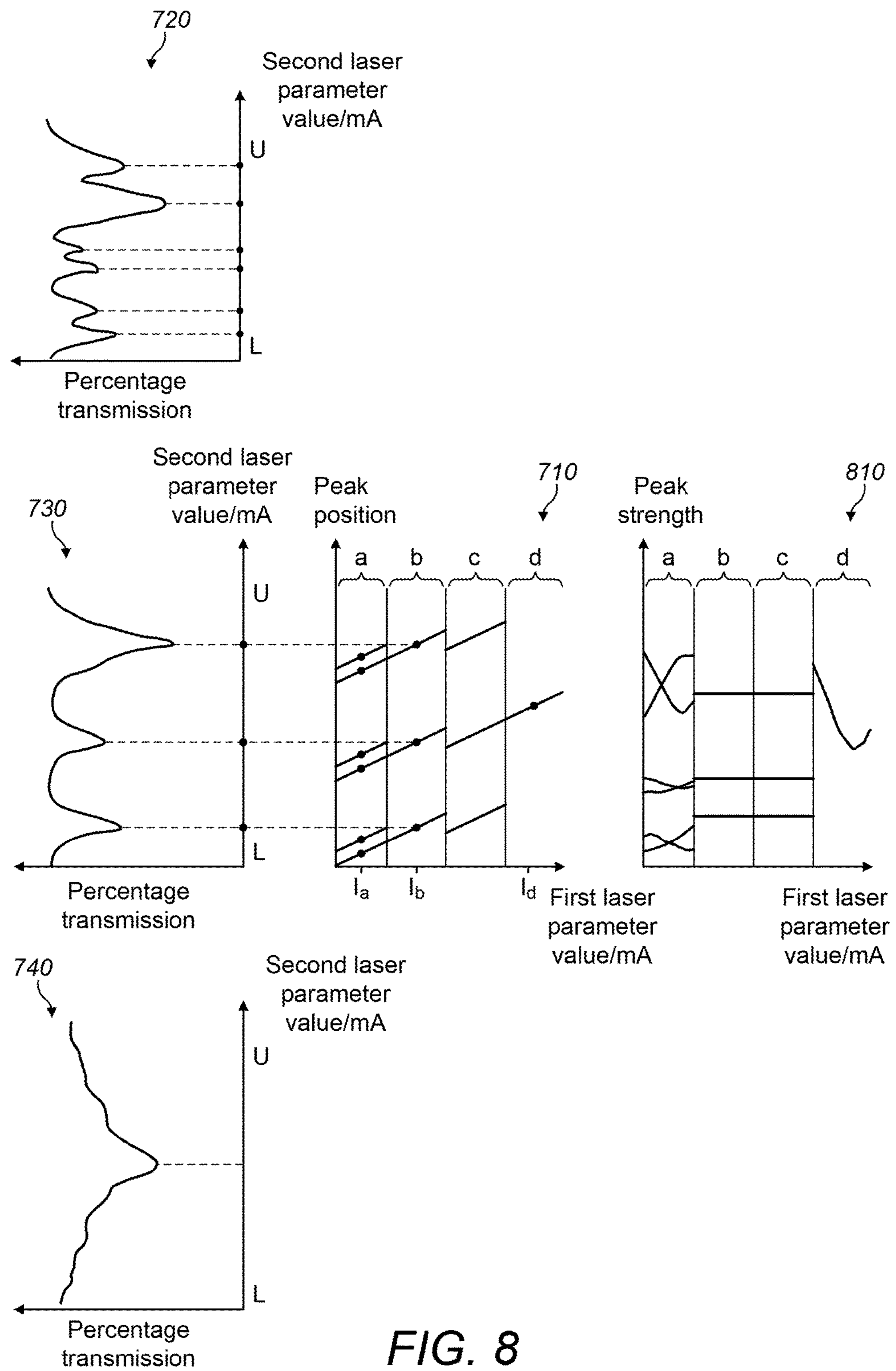
FIG. 8 shows a graphical representation of changes to the identified peak positions with changes to the first laser parameter and changes to the identified peak strengths with changes to the first laser parameter during the method of FIG. 5.

FIG. 8 shows a graphical representation of changes to the identified peak positions with changes to the first laser parameter 112 and a graphical representation of changes to the identified peak strengths with changes to the first laser parameter 112. FIG. 8 is the same as FIG. 7, but includes a further plot 810. Plot 810 is a plot of the peak strength of each identified extremum against the value of the first laser parameter 112. As can be seen, in regions 'a' and 'd', there are strong fluctuations in the peak strength of each of the identified extremum with changes in the value of the first laser parameter 112. This is indicative of the first laser diode 210 multimoding as a result of the distribution of optical power among multiple resonator modes being unstable and changing as the value of the first laser parameter 112 is incremented. However, in regions 'b' and 'c', the peak strength of each of the identified extremum stay the same across all values of the first laser parameter 112. This is because the peak strengths are characteristic of the $CO_2$ quantum mechanical rotational-vibrational state transitions as well as the $CO_2$ isotopologue concentrations, but do not depend on the peak position of the identified extremum. This is indicative of the first laser diode 210 operating at a single-frequency.

Consequently, regions 'b' and 'c' would be identified as ranges of values of the first laser parameter 112 wherein the first laser diode 210 is not multimoding or mode hoping. Consequently, the operating value of the first laser parameter 112 may be set to a value within either of those ranges (as explained earlier).

Typically, two, or three, or four, or more extrema are identified in the spectrum of detected laser light and their peak positions and optionally peak strengths determined for the purpose of performing the process described above.

Thus, it can be seen that regions of multimoding may be identified by considering peak strength, without needing to carry out a comparison between the measured spectrum and a theoretical spectrum of the sample gas in order to determine the number of expected extrema for comparison with the number of identified extrema in the measured spectrum. This may be advantageous in some scenarios where performing a comparison as described above may be too time consuming.

Figure 9:
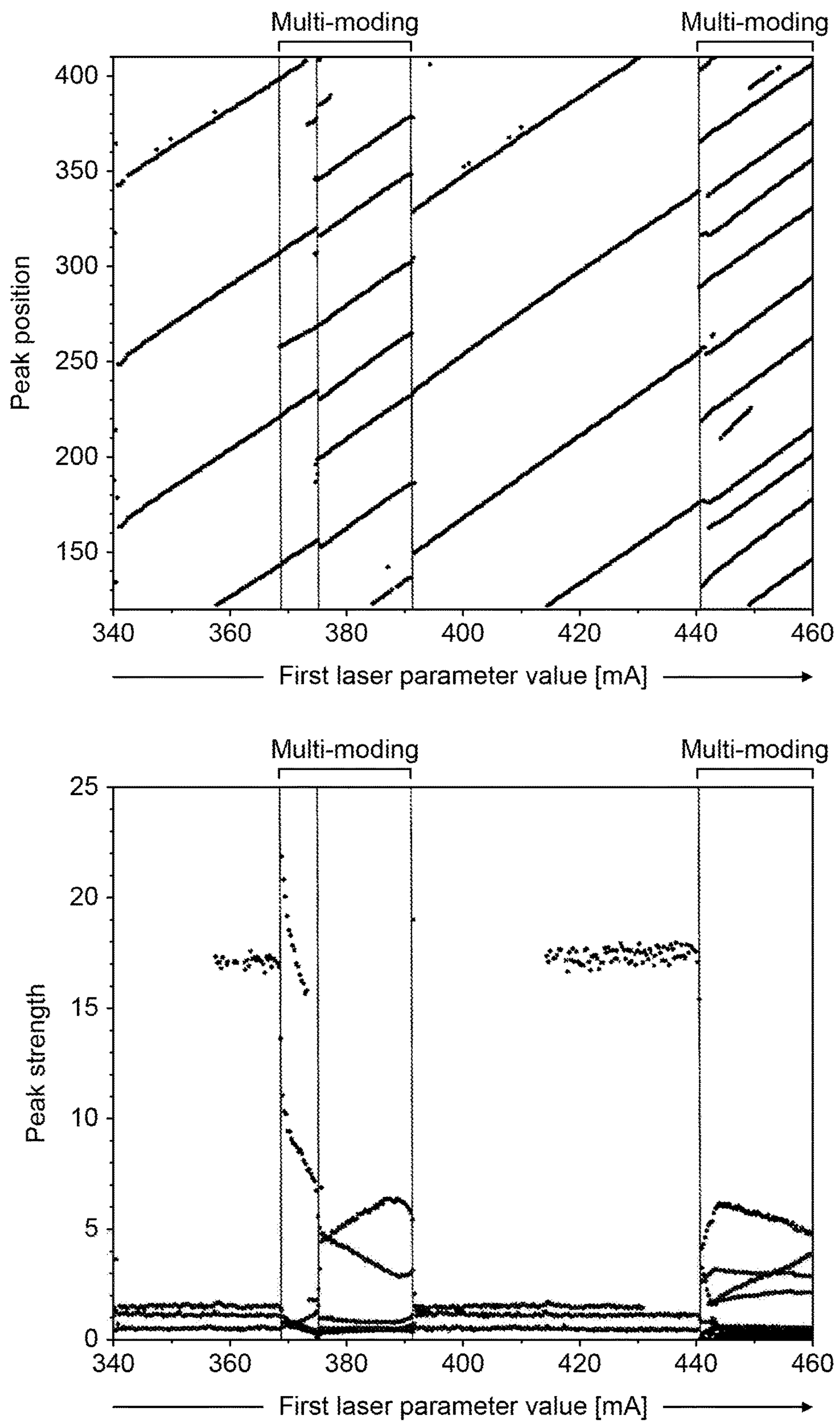
FIG. 9 shows an example experimental plot of changes to the identified peak positions with changes to the first laser parameter and an experimental plot of changes to the identified peak strengths with changes to the first laser parameter during the method of FIG. 5.

FIG. 9 shows an experimental plot of changes in peak position against changes in the first laser parameter value and changes in peak strength against changes in the first laser parameter value, taken by performing the above disclosed process. These experimental plots were taken for a $CO_2$ sample gas. The units of the peak position and peak strength in the plots are arbitrary units (a.u.).

Discontinuities in the trend lines of the peak position plot and regions of multimoding can be seen and separate the plot into different regions. Multimoding regions can readily be seen in the peak strength plot by virtue of changes in the peak strength as the first laser parameter value changes.

It can be seen that there is a first range of first laser parameter values between 340 mA to 369 mA and a second range of first laser parameter values between 391 mA to 440 mA, in each of which there is a continuous trend in changes to peak position with changes to the first laser parameter value, and wherein the peak strength stays the same to within a threshold tolerance (for example, to within ±1%, or ±2%, or ±5%, or ±10%, or ±20%, etc, etc). The threshold tolerance may be set to be a percentage, or to a particular value of peak strength (for example, it may be set to 0.1 mA, or 0.4 mA, or 1 mA, or 1.5 mA, etc), and the size of the threshold may be set in view of experimental accuracy, for example. The second of these ranges is the largest, so the operating value of the first laser parameter 112 may be set to a value in that range.

It can be seen on the plot of peak position that new trend lines appear at currents 357 mA and 414 mA. This is caused by new peak absorptions entering the spectral window as a result of the spectral window moving as the first laser parameter value increases (as explained above in respect of FIG. 6). Likewise, a trend line disappears at a current of 431 mA, which is caused by a peak absorption leaving the spectral window as a result of the spectral window moving as the first laser parameter value increases. It will be appreciated that these do not represent discontinuities in the identified peak positions with changes to the value of the first laser parameter 112 as there is no discontinuity in the plot of the peak position. Likewise, corresponding appearances or disappearances of peak strength can be seen in the peak strength plot in FIG. 9 and do not represent the peak strength values changing by an amount greater than the threshold tolerance because the appearance or disappearance of peak strength is not treated as a change in peak strength.

Figure 10:
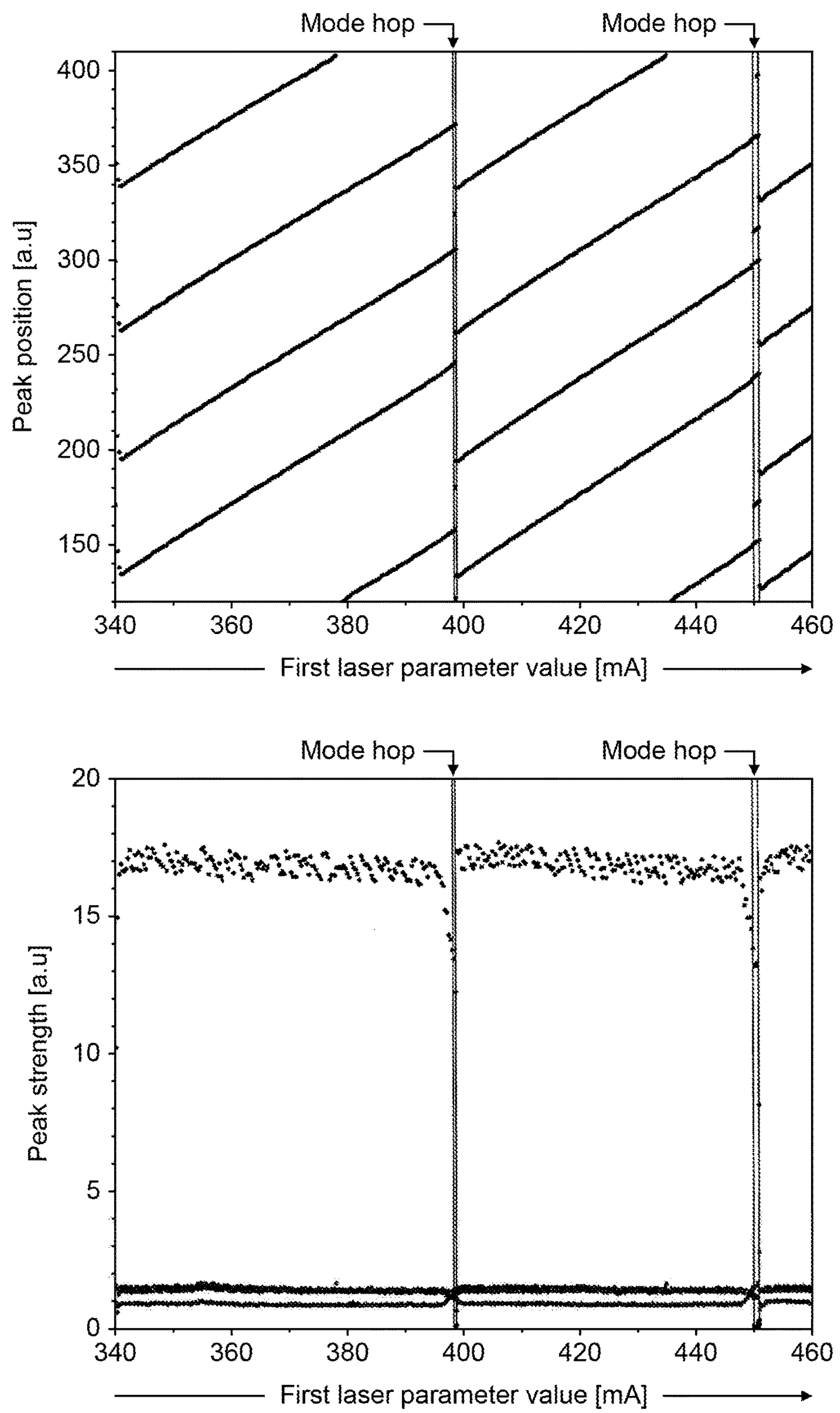
FIG. 10 shows a further example experimental plot of changes to the identified peak positions with changes to the first laser parameter and an experimental plot of changes to the identified peak strengths with changes to the first laser parameter during the method of FIG. 5.

FIG. 10 shows a further experimental plot of changes in peak position against changes in the first laser parameter value and changes in peak strength against changes in the first laser parameter value, taken by performing the above disclosed process. These experimental plots were again taken for a $CO_2$ sample gas, but the laser device 110 used to obtain the plots of FIG. 10 is different to the laser device used to obtain the plots of FIG. 9 (the laser devices may be of the same type, but even then each different laser device may exhibit different characteristics, which result in different peak position and peak strength plots). The units of the peak position and peak strength in the plots are arbitrary units (a.u.).

Discontinuities in the trend lines of the peak position plot may readily be seen and separate the plot into different regions.

It can be seen that there is a first range of first laser parameter values between 340 mA to 398 mA and a second range of first laser parameter values between 398 mA to 450 mA, in each of which there is a continuous trend in changes to peak position with changes to the first laser parameter value, and wherein the peak strength stays the same to within a threshold tolerance (for example, to within ±1%, or ±2%, or ±5%, or ±10%, or ±20%, etc, etc). The threshold tolerance may be set to be a percentage, or to a particular value of peak strength (for example, it may be set to 0.1 mA, or 0.4 mA, or 1 mA, or 1.5 mA, etc), and the size of the threshold may be set in view of experimental accuracy, for example. The first of these ranges is the largest, so the operating value of the first laser parameter 112 may be set to a value in that range. At first laser parameter values of 398 mA and 450 mA, the wavelength of the first laser diode 210 is mode-hopping.

Again, on the plot of peak position it can be seen that new trend lines appear at times, which is caused by new peak absorptions entering the spectral window as a result of the spectral window moving as the first laser parameter value increases (as explained above in respect of FIG. 6). Likewise, at times, trend lines disappear, which is caused by a peak absorption leaving the spectral window as a result of the spectral window moving as the first laser parameter value increases. It will again be appreciated that these do not represent discontinuities in the identified peak positions with changes to the value of the first laser parameter 112 as there is no discontinuity in the plot of the peak position. Likewise, corresponding appearances or disappearances of peak strength can be seen in the peak strength plot in FIG. 10 and do not represent the peak strength values changing by an amount greater than the threshold tolerance because the appearance or disappearance of peak strength is not treated as a change in peak strength.

For the laser device 110 used for FIG. 9, instabilities are predominantly caused by multimoding in the laser light 116. For the laser device 110 used for FIG. 10, instabilities are predominantly caused by mode-hopping in the laser light 116. However, it will be appreciated that for some laser devices, both mode-hopping and multimoding may cause instability.

In the peak strength plots of both FIGS. 9 and 10, some scattering can be seen at higher peak strengths (around a speak strength of 17). This scattering may be caused by imperfections in the peak-find algorithm, which are visible for absorption peaks with larger peak strengths. It will be appreciated that in stable regions, this scattering still remains at a relatively constant value as the first laser parameter value increases, and in regions of multimoding it changes quite rapidly as the first laser parameter value increases. Therefore, the above described process will still function correctly, even where such scattering takes place. For some laser devices 110, and/or for some spectral windows, and/or some peak-find algorithms, such scattering effects may not occur Optionally, after the above described process is performed, it may be repeated, but rather than increasing the value of the first laser parameter in steps S550 and S560 (for example, from 340 to 460 mA), it is decreased (for example, from 460 to 340 mA). At first sight, the peak position and peak strength plots may be expected to look the same as when the value of the first laser parameter 112 is increased.

However, in most cases, wavelength stabilised laser diodes (which is what the first laser diode 210 is in this example) tend to have a hysteretic current tuning characteristic. Consequently, the identified ranges of values of the first laser parameter 112 for which there is a continuous trend in changes to the identified peak positions with changes to the first laser parameter 112 (and optionally for which the peak strength for each of the identified extrema is the same to within a threshold tolerance and/or for which the number of identified extrema correspond to an expected number of extrema) may be different to the case where the value of the first laser parameter 112 was increased.

In this case, Step S570 when the first laser parameter 112 is increased may identify a first range of values of the first laser parameter 112 for which there is a continuous trend in changes to the identified peak positions with changes to the first laser parameter (and optionally for which the peak strength for each of the identified extrema is the same to within a threshold tolerance and/or for which the number of identified extrema correspond to an expected number of extrema). Step S570 when the first laser parameter 112 is decreased may identify a second range of values of the first laser parameter 112 for which there is a continuous trend in changes to the identified peak positions with changes to the first laser parameter 112 (and optionally for which the peak strength for each of the identified extrema is the same to within a threshold tolerance and/or for which the number of identified extrema correspond to an expected number of extrema). The first range and the second range may have different upper and lower limits due to hysteresis, but are likely to overlap for the most-part. Therefore, a final range of values of the first laser parameter 112 is identified, wherein the final range of values comprises all of the values of the first laser parameter 112 that appear in both the first range of values and the second range of values. Alternatively, a final range of values of the first laser parameter 112 is identified, wherein the final range of values comprises all of the values of the first laser parameter 112 that appear in either of the first range of values or the second range of values. In step S580, the operating value of the first laser parameter 112 may be set to be within the identified final range of values of the first laser parameter 112.

In an alternative, process steps S510 to S560 may be performed with increases in the value of the first laser parameter 112, and then they may be repeated with decreases in the value of the first laser parameter 112. The results of both may then be combined in step S570 such that a single peak position plot may be created (wherein each value of the first laser parameter 112 will have at least two corresponding identified peak positions—one from the identified extremum when the first laser parameter value was increased, and the other from the identified extremum when the first laser parameter value was decreased) and a single peak strength plot may be created (wherein each value of the first laser parameter 112 will have at least two corresponding identified peak strengths—one from the identified extremum when the first laser parameter value was increased, and the other from the identified extremum when the first laser parameter value was decreased). Therefore, any values of the first laser parameter 112 at which there is a mode-hop and/or multimoding will be excluded from the identified range, regardless of whether the mode-hop and/or multimoding was detected during the increase in value of the first laser parameter 112 or during the decrease in value of the first laser parameter 112.

It will be appreciated that rather than increasing the value of the first laser parameter 112 and then decreasing the value of the first laser parameter 112, the process may alternatively be performed by decreasing the value of the first laser parameter 112 and then increasing the value of the first laser parameter 112. In a further alternative, the value of the first laser parameter 112 may be decreased without a subsequent process of increasing the value of the first laser parameter 112 (for example, where hysteresis is not a concern).

Various alternatives to the above described aspects of the present disclosure may be appreciated by one with ordinary skill in the art.

For example, rather than the first laser parameter 112 being the injection current to the first laser diode 210 and the second laser parameter 114 being the injection current to the second laser diode 220, a number of alternatives are possible. For example, the following alternative may be implemented:

| | |
|---|---|
| First laser parameter 112 | Temperature of the first laser diode 210 |
| Second laser parameter 114 | Injection current of the second laser diode 220 |

In this example, the operating temperature of the first laser diode 210 would be optimized by the above described process. The injection current of the first laser diode 210 may be set to any suitable value, for example 400 mA.

In a further alternative, the above described process may be carried out wherein the first laser parameter 112 is the injection current of the first laser diode 210, the second laser parameter 114 is the injection current or the temperature of the second laser diode 220, and the first laser temperature is set to a first value. The first laser temperature may then be incremented or decremented and the above described process repeated. This may be repeated a number of times, such that a two-dimensional map of the identified peak positions (and optionally the corresponding measures of peak strength) may be established in order to optimize the operational values of both the injection current and temperature of the first laser diode 210, i.e., identified peak positions (and optionally the corresponding measures of peak strength) are mapped against both the injection current and the temperature of the first laser diode 210. Alternatively, the two-dimensional map of the identified peak positions (and optionally the corresponding measures of peak strength) may be established by choosing the temperature of the first laser diode 210 as the first laser parameter 112 and incrementing or decrementing the first laser injection current after each repetition of the above described process.

In a further alternative, the following may be implemented:

| | |
|---|---|
| First laser parameter 112 | Temperature of the first laser diode 210 |
| Second laser parameter 114 | Temperature of the second laser diode 220 |

In a further alternative, the following may be implemented:

| | |
|---|---|
| First laser parameter 112 | Injection current of the first laser diode 210 |
| Second laser parameter 114 | Temperature of the second laser diode 220 |

In the above examples, the first laser diode 210 is a WS laser diode, and the second laser diode 220 is a DFB laser diode. However, it will be appreciated that the first laser diode 210 may be any form of laser diode and the second laser diode 220 may be any form of laser diode. The first laser diode 210 and the second laser diode 220 may both be of the same type, or they may be of different types.

Furthermore, in the above examples, the wavelength of the light emitted from the laser diode being optimized (the first laser diode 210) is lower than the wavelength of the light emitted from the laser diode being continuously scanned to obtain the spectra (the second laser diode 220). However, it will be appreciated that in an alternative, either laser diode may be optimized while the other laser diode is continuously scanned to obtain the spectra, and that the wavelength of light emitted from the laser diode being optimized may be greater than, or less than, the wavelength of light emitted from the laser diode being continuously scanned to obtain the spectra.

In a further alternative, both the first laser parameter 112 and second laser parameter 114 may apply to the first laser diode 210. For example:

| | |
|---|---|
| First laser parameter 112 | Injection current of the first laser diode 210 |
| Second laser parameter 114 | Temperature of the first laser diode 210 |

Or

| | |
|---|---|
| First laser parameter 112 | Temperature of the first laser diode 210 |
| Second laser parameter 114 | Injection current of the first laser diode 210 |

In these instances, the second laser diode 220 may be held at a constant injection current and temperature.

In a further alternative, both the first laser parameter 112 and second laser parameter 114 may apply to the second laser diode 220. For example:

| | |
|---|---|
| First laser parameter 112 | Injection current of the second laser diode 220 |
| Second laser parameter 114 | Temperature of the second laser diode 220 |

Or

| | |
|---|---|
| First laser parameter 112 | Temperature of the second laser diode 220 |
| Second laser parameter 114 | Injection current of the second laser diode 220 |

In these instances, the first laser diode 210 may be held at a constant injection current and temperature.

In the above example, the laser device 110 comprises a first laser diode 210 and a second laser diode 220. However, in an alternative, it may comprise only one laser diode and the above described process may be used to optimize the operating point of the laser diode. For example, a single laser diode may be used for cavity ring-down spectrometers or off-axis integrated cavity output spectrometers. In this instance, under normal operation of the laser absorption spectrometer 100 when analysing a sample gas, the first laser parameter 112 will be kept fixed and the second laser parameter 114 will be varied (for example, ramped up or down) in order to scan the laser light 116 across absorption peaks of the sample gas. The first laser parameter 112 may be the diode temperature of the laser diode and the second laser parameter 114 may be the injection current to the laser diode. A ramp current (either an increasing ramp or decreasing ramp) may then be applied to the second laser parameter 114 and the temperature value of the first laser parameter 112 may be step-wise incremented (or decremented) as described above. An optimum operating value for the first laser parameter 112 (the laser diode temperature) may thus be identified. In a further alternative, the first laser parameter 112 may be the injection current to the laser diode and the second laser parameter 114 may be the temperature of the laser diode. Furthermore, a two-dimensional map of the identified peak positions (and optionally measures of the corresponding peak strength) may be established in order to optimize the operational values of both the injection current and temperature of the laser diode, as explained above.

Optionally, the laser absorption spectrometer 100 may further comprise an etalon, which may be used as part of the above described process. In this instance, the laser absorption spectrometer 100 may be configured such that the path of the laser light 116 is diverted away (or branched off) from the multipass mirrors 140, through the etalon and into the light intensity detector 120. A sample gas would not be required to be contained within the absorption cell 130. The etalon is configured to have multiple transmission (or reflection) maxima (or minima) within the spectral window of the spectrometer. Thus, the laser light received at the light intensity detector 120 should have a predictable spectrum, wherein the intensity will have maxima (or minima) at wavelengths separated by a defined wavelength interval (this is typically called the free spectral range (FSR) of the etalon). Thus, when the laser light 116 experiences mode-hoping and/or multimoding, this will affect the peak position of extrema and the number of extrema in the laser light transmitted (or reflected) from the etalon in a similar way to that described above. Therefore, mode-hoping may be identified using an etalon by identifying discontinuities in changes to the peak position with changes to the first laser parameter 112. Multimoding may also be identified because the number of extrema that should be identified will be well defined for the etalon, so if the number of identified extrema is different to the expected number, multimoding can be identified. Thus, stable regions can be identified without needing to obtain measures of peak strength for each identified extrema, and without needing to know anything about the sample gas or the exact location of the spectral window on the wavelength axis.

In the above, the measure of light intensity 122 is generally described as the percentage transmission of laser light. However, it may be any measure indicative of a ratio of optical power of light received by the light intensity detector 120 to optical power of light emitted from the laser device 110. For example, it may be the ratio of the optical power of light received by the light intensity detector 120 to optical power of light emitted from the laser device 110, or the ratio of the intensity of light received by the light intensity detector 120 to intensity of light emitted from the laser device 110, or the percentage of optical power or intensity of light emitted from the laser device 110 that is then received at the light intensity detector 120, etc, etc.

Furthermore, in the above, the peak strength is usually described as being the peak area of the extremum. However, it will be appreciated that any suitable measure of peak strength may be used. For example, it may be a value derived from the peak area. Alternatively, it may be the peak height of the absorption peak, which may be the maximum percentage absorption of an absorption peak, or the minimum percentage transmission of an absorption peak, or the minimum or maximum received signal strength, or received light intensity, or detector voltage, or received optical power, etc of an absorption peak. Alternatively, the peak strength may be a value derived from the peak height of the absorption peak. Alternatively, the peak strength may be a value derived from the peak height and the peak area.

In the above, the peak position is the second laser parameter value corresponding to the identified absorption peak. In an alternative, it may be the wavelength of the identified extremum relative to a point in the spectral window, for example the lower wavelength limit $\lambda_L$ or the upper wavelength limit $\lambda_U$. Where it is the wavelength relative to the lower wavelength limit $\lambda_L$, as the value of the first laser parameter 112 increases, the peak position will decrease, resulting in the trend lines in the plot of peak position against first laser parameter value (see plot 710 in FIGS. 7 and 8) having a negative gradient.

Identifying the peak position by relative wavelength may be useful where the first laser diode 210 experiences only mode-hopping and not multimoding. This is because, while multimoding, the first laser diode 210 may emit light at multiple optical frequencies, which may render relative wavelength determinations inaccurate.

Identifying the peak position by second laser parameter value may be useful where the first laser diode 210 experiences both mode-hopping and multimoding. This is because the same range of values of the second laser parameter 114 are applied for each value of the first laser parameter 112, meaning that identifying the peak position using the value of the second laser parameter 114 is absolute. Thus, identifying the peak position by second laser parameter value may be preferable as it will provide an accurate indication of peak position regardless of the type of instability that the first laser diode 210 may experience. Furthermore, it does not require any knowledge, or estimation, of the exact wavelength of the laser light 116, or of the wavelength difference of laser light 116 with respect to the upper wavelength limit $\lambda_U$ or the lower wavelength limit $\lambda_L$.

The laser absorption spectrometer 100 may be any type of laser absorption spectrometer and may be configured to analyse any type of sample gas, for example $H_2O$, $CH_4$ and $N_2O$. Isotope ratio and concentration measurements of these major greenhouse gases can provide valuable information on their sources and sinks. Analysis of $H_2O$ isotope ratios may also help to understand the global water cycle and CH4 isotope ratio analysis may be used to monitor drilling on a hydraulic fracturing site. The light absorption spectrometer 100 may also be used for industrial process monitoring, for example to measure the concentration of hazardous gases like carbon monoxide (CO) or hydrogen chloride (HCl). The light absorption spectrometer 100 may also be used for the detection of hazardous gases like formaldehyde.

In the above, the laser device 110 emits laser light 116 at wavelengths within the mid-infrared spectrum. However, it will be appreciated that the above described process may be applied to any type of laser device 110 emitting laser light 116 at any wavelength. For example, the laser device 110 may emit laser light 116 at a wavelength in the near-infrared region, between 1-2.5 μm, or it may emit laser light 116 at ultra-violet (UV) wavelengths (for example, for the detection of formaldehyde), etc.

In the above, the identified extremum is always a minimum in the measure of light intensity 122. However, it may alternatively be a maximum in the measure of light intensity 122 (for example, where the measure of light intensity 122 is percentage absorption). Furthermore, where a plurality of extrema are identified for each value of the first laser parameter 112, each of the identified extrema may be a maximum or a minimum.

In the above, a continuous ramp of injection current is applied to the second laser parameter 114. Thus, the range of values of the second laser parameter 114 is a continuous range. However, it will be appreciated that discrete changes to the injection current may be applied to the second laser parameter 114, such that the range of values of the second laser parameter 114 are a discrete set of values (for example, a contiguous range).

In FIGS. 7, 8, 9 and 10, discontinuities occur where there is a sudden decrease in the peak position with a small increase in the first laser parameter value. However, discontinuities may occur where there is a sudden increase in the peak position with a small increase in the first laser parameter value. Such discontinuities would still be indicative of mode-hopping in the first laser diode 210.

In the above, the value of the second laser parameter 114 is increased (an upward ramp). However, it will be appreciated that it may alternatively be decreased (for example, a downward ramp, or a repeated, discrete reduction in value of the second laser parameter 114). In this instance, decreasing the value of the second laser parameter 114 would result in an increase in the wavelength of laser light 116. Nevertheless, the spectral window of laser light 116 would still be the same, the only difference being that the wavelength of laser light would increase from the lower wavelength limit $\lambda_L$ to the upper wavelength limit $\lambda_U$, owing to the downward ramp of the wavelength of light emitted from the second laser diode 220.

In the above description, the laser device 110 is a DFG type laser, wherein the optical frequency of the laser light 116 is the difference between the optical frequencies of the first laser diode 210 and the second laser diode 220 (the frequency of the laser light emitted from the second laser diode 220 being subtracted from the frequency of the laser light emitted from the first laser diode 210). In one example described above, the first laser parameter 112 is the temperature of the first laser diode 210, and the second laser parameter 114 is the injection current of the same laser diode 210 (rather than the injection current of the second laser diode 220). In this case, as the wavelength of the first laser diode is ramped up (by an upward ramp in the value of the second laser parameter 114), the wavelength of laser light 116 will also ramp up. Therefore, the ramp in plot 330 of FIG. 3 will have a positive gradient, with the wavelength of laser light 116 increasing from the lower wavelength limit $\lambda_L$ to the upper wavelength limit $\lambda_U$ as the second laser parameter is increased from a lower value L to an upper value U. Likewise, as the value of the first laser parameter 112 (temperature of the first laser diode) is increased, the wavelength of laser light 116 will also increase. Therefore, like in the plots shown in FIG. 6, the spectral window will shift to the right as the value of the first laser parameter 112 is increased. However, unlike in the plots shown in FIG. 6, the direction of increase of the second laser parameter value from L to U will go from left to right, as a consequence of increases in the value of the second laser parameter resulting in an increase in the wavelength of the laser light 116. The identified extremum 690 therefore will occur at lower values of the second laser parameter 114 as the first laser parameter value increases. Consequently, the plots of peak position against first laser parameter value will look very similar to that of plot 710 in FIGS. 7 and 8, only the trend lines will have a negative gradient, rather than the positive gradient shown in plot 710. Nevertheless, multimoding and/or mode-hopping will still be identifiable as described above, such that the above described process of optimizing the operating value of the laser device 110 works effectively, regardless of the particular choice of the first and second laser parameters 112 and 114, respectively, in a DFG type laser device.

Thus, it will be appreciated that the trend lines in the plots of peak position against first laser parameter value may have a positive gradient or a negative gradient, depending on the type of laser device, which laser diode in the laser device is the first laser diode and which is the second laser diode (where the laser device comprises two laser diodes) and/or what the first and second laser parameters are. Regardless, multimoding and/or mode-hopping will still be identifiable as described above, such that the above described process of optimizing the operating value of the laser device 110 works effectively.

Furthermore, the laser device 110 may alternatively be a sum frequency generation (SFG) type laser, wherein the optical frequency of the laser light 116 is the sum of the optical frequencies of the first laser diode 210 and the second laser diode 220. In this case, as the wavelength of the second laser diode is ramped up (by an upward ramp in the value of the second laser parameter 114), the wavelength of laser light 116 will also ramp up. Therefore, the ramp in plot 330 of FIG. 3 will have a positive gradient, with the wavelength of laser light 116 increasing from the lower wavelength limit $\lambda_L$ to the upper wavelength limit $\lambda_U$ with time. Likewise, as the value of the first laser parameter 112 is increased, the wavelength of laser light 116 will also increase. Therefore, in the plots shown in FIG. 6, the spectral window will shift to the right as the value of the first laser parameter 112 is increased (as is shown in FIG. 6). However, the direction of increase of the second laser parameter value from L to U will go from left to right (rather than right to left, as shown in FIG. 6), as a consequence of increases in the value of the second laser parameter resulting in an increase in the wavelength of the laser light 116. Consequently, the plots of peak position against first laser parameter value will look very similar to that of plot 710 in FIGS. 7 and 8, only the trend lines will have a negative gradient, rather than the positive gradient shown in plot 710. Nevertheless, multimoding and/or mode-hopping will still be identifiable as described above, such that the above described process of optimizing the operating value of the laser device 110 works effectively, regardless of whether the laser device 110 is of an SFG or a DFG type.

Furthermore, where the laser device 110 comprises a single laser diode, increases in either of the first laser parameter value and the second laser parameter value results in an increase in the wavelength of the laser light 116. This situation is the same as for an SFG type laser, such that the explanation above for an SFG type laser applies equally to a laser device 110 comprising a single laser diode.

In the above disclosed aspects, the laser device 110 comprises a first laser diode 210 and a second laser diode 220. However, the laser device 110 may comprise one or more lasers of any type, for example any type of gas laser, solid-state laser, semiconductor laser, a fiber-laser etc, and the above disclosed process be used to optimize the operating values of any one or more of those lasers.

In the above, the controller 170 receives the measure of light intensity 122, adjusts the values of the first laser parameter 112 and the second laser parameter 114, identifies the optimum value of the first laser parameter 112 and applies it to the laser device 110. However, it will be appreciated that the process may be performed by any electronic device, which may or may not form part of the laser absorption spectrometer 100. For example, it may be performed on a desktop computer, or a laptop computer, or a tablet computer, or a mobile device such as a smartphone, that is configured to obtain, for each of a plurality of values of the first laser parameter 112, a measure of light intensity 122 received at the light intensity detector 120 across a range of values of the second laser parameter 114. This may be obtained via a wired or wireless coupling with the controller 170. The electronic device may be configured to adjust the values of the first and/or second laser parameters as part of the process, or the adjustment of the values of the first and/or second laser parameters may be performed by the controller 170 (for example, the controller 170 may be configured to perform the adjustments of the first and/or second laser parameters as described above and then simply provide the measure of light intensity 122 data to the electronic device such that the electronic device may carry out the analysis described above in order to determine the optimum value of the first laser parameter 112). In setting the operating value of the first laser parameter 112, the electronic device may be configured to apply the operating value to the laser device 110, and/or display the operating value that it has set so that an operator of the laser absorption spectrometer may apply it to the laser device 110, and/or pass the operating value that it has set to the controller 170 so that the controller 170 may apply it to the laser device 110.

The electronic device may comprise a processor and memory storing a software program, wherein the software program, when executed by the processor, causes the processor and thus the electronic device, to perform the above disclosed method. Alternatively, the electronic device may be configured to perform the above disclosed method by any other means, for example it may comprise programmable logic configured to perform the above disclosed method.

The present disclosure also provides a software program (or a computer program) configured to perform the above disclosed method of the present disclosure when executed on the processor of an electronic device. It will be appreciated that a storage medium and a transmission medium carrying the computer program form aspects of the invention. The computer program may have one or more program instructions, or program code, which, when executed by a computer carries out the above disclosed aspects of the invention. The term "program" or "software" as used herein, may be a sequence of instructions designed for execution on a computer system, and may include a subroutine, a function, a procedure, a module, an object method, an object implementation, an executable application, an applet, a servlet, source code, object code, a shared library, a dynamic linked library, and/or other sequences of instructions designed for execution on a computer system. The storage medium may be a magnetic disc (such as a hard drive or a floppy disc), an optical disc (such as a CD-ROM, a DVD-ROM or a BluRay disc), or a memory (such as a ROM, a RAM, EEPROM, EPROM, Flash memory or a portable/removable memory device), etc. The transmission medium may be a communications signal, a data broadcast, a communications link between two or more computers, etc.

Thus, it can be seen that the present disclosure provides a technique for optimizing with respect to stability, at any time during the lifetime of the laser absorption spectrometer 100, the operating point of the laser device 110. Thus, as the laser device 110 ages, its optimum operating point may be identified to ensure that it remains in a stable, single-frequency region, thereby maintaining the accuracy of measurements from the laser absorption spectrometer 100 over time.

The technique provided in the present disclosure requires no additional hardware and is not dependent on using a particular calibrant gases with particular molecular absorption peaks (i.e., any sample gas with at least one absorption peak in the spectral window of the spectrometer may be used, and it is not necessary to know anything more in advance about the molecular absorption peaks of that gas). The process may utilise a peak find algorithm, and optionally also a peak-fit algorithm, which the controller 170 and/or electronic device is likely already to have for sample gas analysis purposes, so existing software modules may be re-used.

Advantageously, the above described process of optimizing the operating value of the first laser parameter 112 can be performed in a short time, for example, in less than 10 minutes. The process could be arranged so as to run on the laser absorption spectrometer 100 on a regular basis, the regularity of which could be chosen by the user. For example, the process could be arranged to be automatically run once a month, or more or less frequently than this. In this way, the operating point of the laser device 110 can be automatically maintained at or close to optimum as the laser device 110 ages.

The invention claimed is:

1. A method for optimizing an operating value of a first laser parameter of a laser device in a laser absorption spectrometer, wherein the wavelength of laser light emitted from the laser device is variable by adjusting either of the first laser parameter and a second laser parameter of the laser device, and wherein the laser absorption spectrometer includes a light intensity detector configured to measure the intensity of laser light received from the laser device, the method comprising:

for each of a plurality of values of the first laser parameter:

obtaining a measure of light intensity received at the light intensity detector across a range of values of the second laser parameter;

identifying an extremum in the measure of light intensity; and identifying a peak position for the extremum;

identifying a range of values of the first laser parameter within the plurality of values of the first laser parameter for which there is a continuous trend in changes to the identified peak position with changes to the first laser parameter; and setting the operating value of the first laser parameter to be within the identified range of values of the first laser parameter.

2. The method of claim 1, wherein the identified range of values of the first laser parameter is a range of values of the first laser parameter within the plurality of values of the first laser parameter for which a function defining the identified peak positions with changes to the first laser parameter is a continuous function.

3. The method of claim 1, wherein the continuous trend is a linear continuous trend.

4. The method of claim 1, wherein the identified peak position is based at least in part on a value of the second laser parameter corresponding to the identified extremum.

5. The method claim 4, wherein the identified peak position is the value of the second laser parameter corresponding to the identified extremum.

6. The method of claim 1, wherein a peak strength for each of the identified extrema is the same to within a threshold tolerance.

7. The method of claim 6, wherein the peak strength is based at least in part on at least one of a peak height and/or a peak area.

8. The method of claim 1, wherein a number of identified extrema at each of the plurality of values of the first laser parameter corresponds with an expected number of extrema.

9. The method of claim 1, wherein the extremum is identified using a peak-find algorithm.

10. The method of claim 1, wherein two or more ranges of values of the first laser parameter are identified within the plurality of further values of the first laser parameter, the method further comprising:

setting the operating value of the first laser parameter to be within the largest of the two or more identified ranges of values of the first laser parameter.

11. The method of claim 1, wherein the operating value of the first laser parameter is set to a value that is closer to a centre of the identified range of values of the first laser parameter than it is to either limit of the identified range of values of the first laser parameter.

12. The method of claim 1, wherein the operating value of the first laser parameter is set to within a tolerance threshold of the centre of the identified range of values of the first laser parameter.

13. The method of claim 1, wherein the laser device comprises a laser diode, and wherein:

the first laser parameter is a temperature of the laser diode and the second laser parameter is an injection current of the laser diode; or the first laser parameter is an injection current of the laser diode and the second laser parameter is a temperature of the laser diode.

14. The method of claim 1, wherein the laser device comprises a first laser diode and a second laser diode configured together to produce the laser light emitted from the laser device, the first laser parameter being a parameter of the first laser diode and the second laser parameter being a parameter of the second laser diode.

15. The method of claim 14, wherein the first laser parameter is an injection current to the first laser diode and the second laser parameter is an injection current to the second laser diode.

16. The method of claim 14, wherein the first laser parameter is a temperature of the first laser diode and the second laser parameter is an injection current to the second laser diode.

17. The method of claim 14, wherein the first laser diode is a wavelength stabilised laser diode and the second laser diode is a distributed feedback laser diode.

18. The method of claim 1, wherein the measure of light intensity received at the light intensity detector is indicative of a ratio of optical power of light received by the light intensity detector to optical power of light emitted from the laser device.

19. The method of claim 1, wherein the laser absorption spectrometer further comprises an absorption cell suitable for containing a sample gas, the laser absorption spectrometer being configured such that, in use, laser light emitted from the laser device passes through an absorption cell to the light intensity detector.

20. The method of claim 19, wherein, in use, laser light emitted from the laser device passes through the absorption cell containing the sample gas to the light intensity detector and the identified extremum corresponds to an absorption peak of the sample gas.

21. The method of claim 1, wherein the laser absorption spectrometer further comprises an etalon and an absorption cell suitable for containing a sample gas, the laser absorption spectrometer being configured such that, in use, laser light emitted from the laser device passes through the etalon, or through the absorption cell, to the light intensity detector.

22. The method of claim 1, further comprising:

for each of the plurality of values of the first laser parameter:

identifying a plurality of extrema in the measure of light intensity; and identifying for each of the plurality of extrema a respective peak position; wherein the identified range of values of the first laser parameter is a range of values of the first laser parameter within the plurality of values of the first laser parameter for which there is a continuous trend in changes to the peak position in the identified plurality of peak positions with changes to the first laser parameter.

* * * * *